United States Patent
Zhang et al.

(10) Patent No.: US 11,998,432 B2
(45) Date of Patent: Jun. 4, 2024

(54) METHOD OF MANUFACTURING A FOAM AND FIBER COMPOSITE

(71) Applicant: Kimberly-Clark Worldwide, Inc., Neenah, WI (US)

(72) Inventors: Jun G. Zhang, Appleton, WI (US); April Montoya Vaverka, Roswell, GA (US); Palani Raj Ramaswami Wallajapet, Neenah, WI (US); Richmond R. Cohen, Appleton, WI (US); Mary Alice Berceau, De Pere, WI (US); Joseph K. Baker, Cumming, GA (US); Udaykumar Raval, Cumming, GA (US); David Glen Biggs, New London, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1569 days.

(21) Appl. No.: 16/310,973

(22) PCT Filed: Sep. 9, 2016

(86) PCT No.: PCT/US2016/050996
§ 371 (c)(1),
(2) Date: Dec. 18, 2018

(87) PCT Pub. No.: WO2018/004708
PCT Pub. Date: Jan. 4, 2018

(65) Prior Publication Data
US 2020/0306107 A1    Oct. 1, 2020

Related U.S. Application Data

(60) Provisional application No. 62/357,015, filed on Jun. 30, 2016.

(51) Int. Cl.
*A61F 13/15*    (2006.01)
*A61F 13/53*    (2006.01)
(Continued)

(52) U.S. Cl.
CPC ........ *A61F 13/53* (2013.01); *A61F 13/15203* (2013.01); *A61F 13/15577* (2013.01);
(Continued)

(58) Field of Classification Search
CPC .......... A61F 13/15203; A61F 13/15577; A61F 13/53; A61F 13/534; A61F 2013/15406; A61F 2013/530802
See application file for complete search history.

(56) References Cited

U.S. PATENT DOCUMENTS 2,896,618 A    7/1959  Schaefer
3,122,140 A    2/1964  Crowe, Jr.
(Continued)

FOREIGN PATENT DOCUMENTS

CN    1070924 A    4/1993
CN    101166625 A    4/2008
(Continued)

OTHER PUBLICATIONS

Co-pending U.S. Appl. No. 16/310,957, filed Dec. 18, 2018, by Zhang et al. for "Foam and Fiber Composite."
(Continued)

*Primary Examiner* — Catharine L Anderson
(74) *Attorney, Agent, or Firm* — KIMBERLY-CLARK WORLDWIDE, INC.

(57) ABSTRACT

The foam and fiber composite can provide an absorbent article with improved dryness and an improved liquid distribution capability. The foam and fiber composite can be formed from at least two materials. The first material is an open cell foam material and the second material is a fibrous (Continued)

material. A plurality of the fibers forming the fibrous material can be fluid inserted into the open cell foam material thereby forming the foam and fiber composite. In various embodiments, the foam and fiber composite can be incorporated into an absorbent article as a component of an absorbent system located between a topsheet layer and a backsheet layer of the absorbent article.

18 Claims, 10 Drawing Sheets

(51) Int. Cl.
 B32B 5/06 (2006.01)
 B32B 5/18 (2006.01)
 B32B 5/24 (2006.01)
 B32B 37/18 (2006.01)
 B32B 37/10 (2006.01)
 C08L 75/06 (2006.01)

(52) U.S. Cl.
 CPC ............ *B32B 5/06* (2013.01); *B32B 5/18* (2013.01); *B32B 5/245* (2013.01); *B32B 37/182* (2013.01); *A61F 2013/15406* (2013.01); *B32B 2037/1072* (2013.01); *B32B 2262/062* (2013.01); *B32B 2266/0264* (2013.01); *B32B 2266/0278* (2013.01); *B32B 2555/02* (2013.01); *C08L 75/06* (2013.01); *C08L 2203/14* (2013.01); *C08L 2205/16* (2013.01)

(56) References Cited

U.S. PATENT DOCUMENTS

| | | | |
|---|---|---|---|
| 3,122,142 A | 2/1964 | Crowe, Jr. |
| 3,229,691 A | 1/1966 | Crowe, Jr. et al. |
| 3,451,885 A | 6/1969 | Klein |
| 3,532,588 A | 10/1970 | Newman et al. |
| 3,837,999 A | 9/1974 | Chung et al. |
| 3,862,522 A | 1/1975 | Mednick |
| 4,235,237 A | 11/1980 | Mesek et al. |
| 4,532,173 A | 7/1985 | Suzuki et al. |
| 4,537,819 A | 8/1985 | Schortmann et al. |
| 4,830,905 A | 5/1989 | Gulya et al. |
| 4,879,170 A | 11/1989 | Radwanski et al. |
| 5,151,091 A | 9/1992 | Glaug et al. |
| 5,853,402 A | 12/1998 | Faulks et al. |
| 6,030,559 A | 2/2000 | Barry et al. |
| 6,399,854 B1 | 6/2002 | Vartiainen |
| 6,423,046 B1 | 7/2002 | Fujioka et al. |
| 6,551,295 B1 | 4/2003 | Schmidt et al. |
| 6,657,101 B1 | 12/2003 | Malmgren et al. |
| 6,828,354 B2 | 12/2004 | Hähnle et al. |
| 7,037,298 B2 | 5/2006 | Ohshima et al. |
| 8,410,331 B2 | 4/2013 | Janusson et al. |
| 8,519,211 B2 | 8/2013 | Johannison et al. |
| 2002/0197442 A1 | 12/2002 | Wyner et al. |
| 2003/0093050 A1 | 5/2003 | Baker |
| 2003/0097103 A1 | 5/2003 | Horney et al. |
| 2003/0220039 A1 | 11/2003 | Chen et al. |
| 2004/0142160 A1 | 7/2004 | Cannon et al. |
| 2005/0124709 A1 | 6/2005 | Krueger et al. |
| 2005/0287192 A1 | 12/2005 | Nygren et al. |
| 2006/0148917 A1 | 7/2006 | Radwanski et al. |
| 2008/0221538 A1 | 9/2008 | Zhao et al. |
| 2014/0295134 A1 | 10/2014 | Wood et al. |
| 2015/0080823 A1 | 3/2015 | Thompson et al. |
| 2015/0313770 A1 | 11/2015 | Hubbard, Jr. et al. |
| 2016/0319470 A1 | 11/2016 | Jenkins et al. |
| 2016/0332418 A1 | 11/2016 | Jenkins et al. |

FOREIGN PATENT DOCUMENTS

| | | |
|---|---|---|
| CN | 101327156 A | 12/2008 |
| CN | 103007333 A | 4/2013 |
| CN | 103203905 A | 7/2013 |
| CN | 104497473 A | 4/2015 |
| DE | 102010047105 A1 | 4/2012 |
| GB | 2464970 A | 5/2010 |
| JP | 2007327005 A | 12/2007 |
| WO | 9856430 A2 | 12/1998 |
| WO | 0013637 A2 | 3/2000 |
| WO | 0078369 A1 | 12/2000 |
| WO | 2011128790 A2 | 10/2011 |
| WO | 12156691 A1 | 11/2012 |
| WO | 2013070909 A1 | 5/2013 |

OTHER PUBLICATIONS

Co-pending U.S. Appl. No. 16/310,983, filed Dec. 18, 2018, by Zhang et al. for "Absorbent Article with a Foam and Fiber Composite."

Co-pending U.S. Appl. No. 16/310,992, filed Dec. 18, 2018, by Zhang et al. for "Foam and Fiber Composite."

METHOD OF MANUFACTURING A FOAM AND FIBER COMPOSITE

RELATED APPLICATIONS

The present application claims priority to U.S. Provisional Application No. 62/357,015, filed Jun. 30, 2016, the contents of which are hereby incorporated by reference in a manner consistent with the present application.

BACKGROUND OF THE DISCLOSURE

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, diapers, training pants, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layers. In use, some of these products, such as, for example, feminine pads, sanitary napkins, pantiliners, panty shields, and some incontinence devices, are positioned in the crotch portion of an undergarment for absorption of the body exudates and a garment attachment adhesive on the backsheet layer can be used to attach the product to the undergarment and protect the undergarment from staining. Other products, such as, for example, the diapers, training pants, and some incontinence devices are configured to be positioned between the legs of the wearer and to further encircle the lower torso of the wearer. If the body exudates to be absorbed cannot be efficiently spread through the absorbent article they may run off the edge of the absorbent article causing leakage and staining.

A related problem is that some absorbent cores, while readily sufficient in capturing body exudates, may be insufficient in locking away the body exudates. In some instances, some of the body exudates which have been captured by the absorbent core may migrate back to the topsheet layer of the absorbent article after having initially been pulled away from the topsheet layer by the absorbent core. The wearer of the absorbent article may feel uncomfortable in such circumstances as the migration of body exudates back to the topsheet layer can result in a feeling of wetness at the topsheet layer of the absorbent article. The feeling of wetness at the topsheet layer may result in the wearer feeling unsure about the absorbent article and prompt concerns about embarrassment and staining.

As a result, there remains a need for an improved product, such as an absorbent article, that has improved dryness and an improved liquid distribution capability.

SUMMARY OF THE DISCLOSURE

In various embodiments, a process for manufacturing a foam and fiber composite can have the steps of providing a foam material comprising a first planar surface and a second planar surface; providing a fluid treatment device having a pressurized fluid jet capable of emitting a pressurized fluid stream of fluid from the pressurized fluid jet in a direction towards the foam material; directing the pressurized fluid stream of fluid in a direction from the pressured fluid jet of the fluid treatment device towards the first planar surface of the foam material; providing a fibrous material comprising a plurality of individual fibers and layering the fibrous material onto the first planar surface of the foam material to form a layered composite; providing a fluid insertion device having a pressurized fluid jet capable of emitting a pressurized fluid stream of fluid from the pressurized fluid jet in a direction towards the layered composite; and directing the pressurized fluid stream of fluid in a direction from the pressurized fluid jet of the fluid insertion device towards the fibrous material of the layered composite to cause a portion of the plurality of individual fibers of the fibrous material to be directed into the foam material to form the foam and fiber composite.

In various embodiments the process can further have the step of providing a support belt. In various embodiments, the support belt is a single plain weave foraminous wire.

In various embodiments, a strain rate is maintained on the foam material at less than about 5% strain.

In various embodiments, the pressure of the fluid of the pressurized fluid streams of the fluid treatment device is from about 150 psi to about 1000 psi. In various embodiments, the pressure of the fluid of the pressurized fluid streams of the fluid insertion device is from about 70 psi to about 1000 psi.

In various embodiments, the foam material has a permeability to air flow of less than about 200 CFM prior to contact by the fluid of the pressurized fluid streams of the fluid treatment device and a permeability to air flow of greater than about 600 CFM following contact by the fluid of the pressurized fluid streams of the fluid treatment device.

In various embodiments, a plurality of individual fibers are present at the second planar surface of the foam material following contact by the fluid of the pressurized fluid streams of the fluid insertion device.

In various embodiments, the foam material has an elongation at break of less than about 200%. In various embodiments, the foam material has an elongation at break of from about 80% to about 200%.

In various embodiments, a foam and fiber composite is manufactured according to the process described herein. In various embodiments, the foam and fiber composite has a permeability to air flow greater than about 300 CFM. In various embodiments, the foam material has a height measured from the first planar surface to the second planar surface and from about 15% to about 25% of fibers are present throughout the height of the foam material.

In various embodiments, an absorbent article can have a topsheet layer, a backsheet layer, and an absorbent system positioned between the topsheet layer and the backsheet layer, wherein the absorbent system comprises the foam and fiber composite manufactured according to the process described herein.

In various embodiments, the foam material is a polyester polyurethane foam. In various embodiments, the fibers of the fibrous material are cellulosic fibers. In various embodiments, the total basis weight of the foam and fiber composite is from about 20 gsm to about 250 gsm. In various embodiments, the basis weight of the second material is at least about 10% of the total basis weight of the foam and fiber composite.

Figure 1:
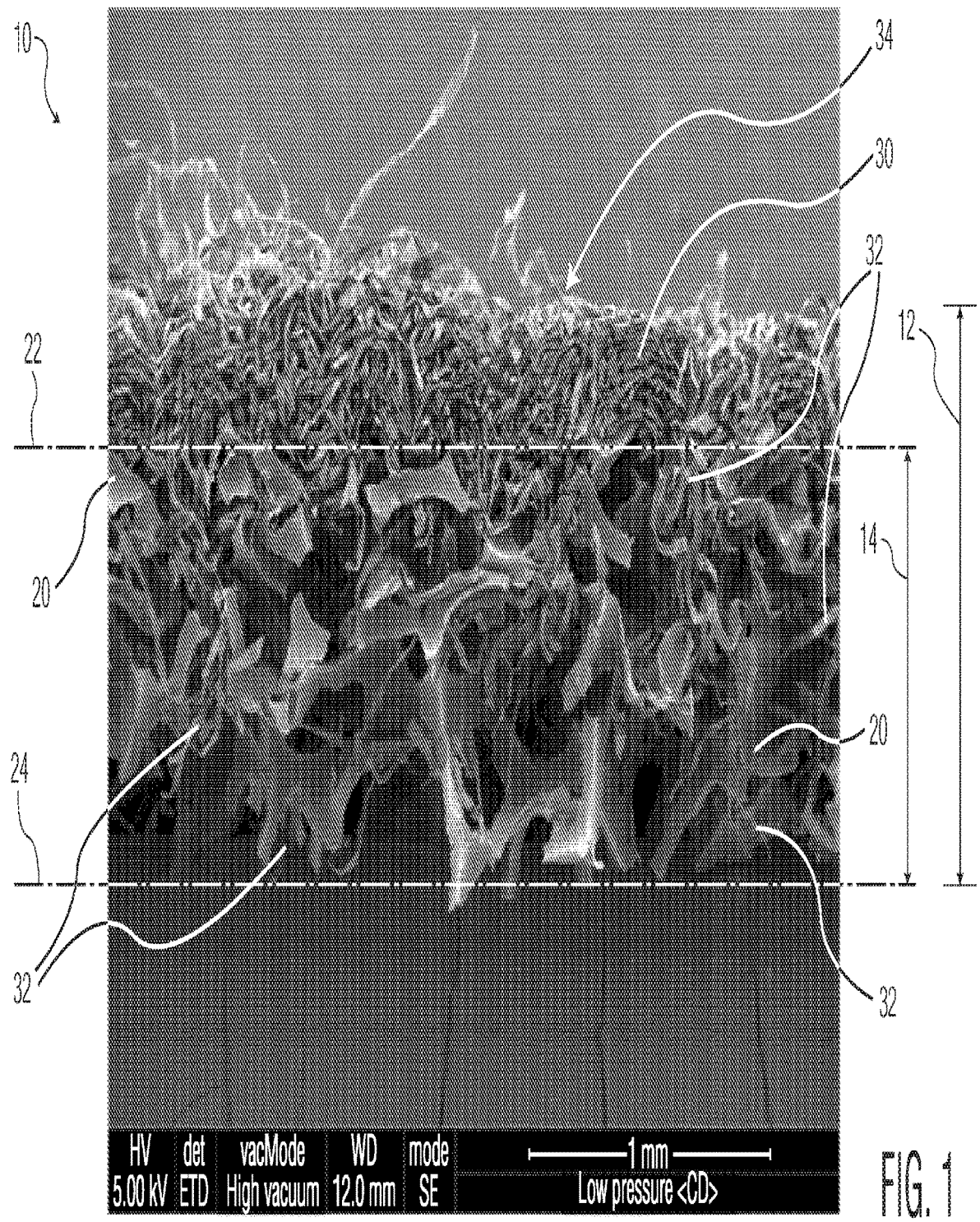
FIG. 1 is a photomicrograph of a cross-sectional view of a portion of a foam and fiber composite.

Repeat use of reference characters in the present specification and drawings is intended to represent the same or analogous features or elements of the disclosure.

DETAILED DESCRIPTION OF THE DISCLOSURE

The present disclosure is generally directed towards a foam and fiber composite, a method of manufacturing the foam and fiber composite, and the incorporation of the foam and fiber composite into an absorbent article. The foam and fiber composite, when utilized in an absorbent article, can provide the absorbent article with improved dryness and an improved liquid distribution capability. The foam and fiber composite can be formed of at least two materials. The first material is an open cell foam material and the second material is a fibrous material. A plurality of the fibers forming the fibrous material can be fluid inserted into the open cell foam material thereby forming the foam and fiber composite. In various embodiments, the foam and fiber composite can be incorporated into an absorbent article as a component of an absorbent system located between a topsheet layer and a backsheet layer of the absorbent article. The plurality of fibers which have been fluid inserted into the open cell foam material can provide a hydrophilic pathway through the open cell foam material to direct body exudate away from the topsheet layer of the absorbent article and through the open cell foam material from the body facing side of the open cell foam material to the garment facing side of the open cell foam material. Thus, the foam and fiber composite can provide improved dryness to the absorbent system of an absorbent article. The material composition of the open cell foam material can reduce and/or prevent the migration of body exudates back to the topsheet layer of the absorbent article. For example, in various embodiments, the open cell foam material can be hydrophobic. The fibers which have been fluid inserted into the foam material can, therefore, direct body exudate flow through the foam material and, if present, into a lower layer of the absorbent system of the absorbent article. As the foam material can be hydrophobic the body exudate is less capable of migrating back through the foam material towards the topsheet layer. The fibers can be oriented in such a manner that they can distribute the trapped body exudates to additional layer(s), if present, of the absorbent system. The foam and fiber composite can, therefore, provide improved distribution capability to the absorbent article.

Definitions:

As used herein, the term "absorbent article" refers herein to a garment or other end-use personal care absorbent article, including, but not limited to, catamenial products, such as sanitary napkins, feminine pads, pantiliners, and panty shields, incontinence devices, diapers, training pants, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Foam and Fiber Composite:

The result of the fluid insertion manufacturing process described herein is the generation of a foam and fiber composite. The foam and fiber composite of the present disclosure can provide an absorbent article with improved dryness and an improved liquid distribution capability. The foam and fiber composite can be formed from at least two materials. The first material is an open cell foam material and the second material is a fibrous material. A plurality of the fibers forming the fibrous material can be fluid inserted into the open cell foam material thereby forming the foam and fiber composite. In various embodiments, the foam and fiber composite can be incorporated into an absorbent article as a component of an absorbent system located between a topsheet layer and a backsheet layer of the absorbent article. The plurality of fibers which have been fluid inserted into the open cell foam material can provide a hydrophilic pathway through the open cell foam material to direct body exudates through the open cell foam material from the body facing side of the open cell foam material to the garment facing side of the open cell foam material. The open cell foam material can reduce and/or prevent the migration of body exudates back to the topsheet layer of the absorbent article.

FIG. 1 provides a photomicrograph of a cross-sectional view of a portion of a foam and fiber composite 10. The photomicrograph was taken by scanning electron microscope at a magnification of 100×. As is visible in FIG. 1, the foam and fiber composite 10 can be formed of an open cell foam material 20 and a fibrous material 30. The foam material 20 can have a first planar surface 22 and a second planar surface 24. In FIG. 1 each planar surface, 22 and 24, have been delineated by the corresponding broken lines for visual clarity. A layer of fibrous material 30 is in contact with one of the planar surfaces, such as planar surface 22, of the foam material 20. The layer of fibrous material 30 is formed from a plurality of individual fibers 32. As is visible in the foam and fiber composite 10 shown in FIG. 1, a portion of the individual fibers 32 extend from the layer of the fibrous material 30 and through the foam material 20 from the first planar surface 22 of the foam material 20 to the second planar surface 24 of the foam material 20.

The foam and fiber composite 10 can have a total height 12 as measured from the exterior surface 34 of the fibrous material 30 to the second planar surface 24 of the foam material 20. The foam and fiber composite 10 can have a sub-height 14 as measured from the first planar surface 22 to the second planar surface 24 of the foam material 20. Each of the total height 12 and sub-height 14 are measurements of distance between the two indicated surfaces. In various embodiments, the total height 12 of the foam and fiber composite 10 can be from about 0.5, 0.75, or 1 mm to about 4, 6, or 10 mm.

The fluid insertion manufacturing process described herein results in a foam and fiber composite 10 wherein a portion of the fibers 32 from the fibrous material 30 can be present in the structure of the foam material 20. Image analysis can be utilized to calculate the proportion of fiber 32 within the foam material 20. In various embodiments, the imaging analysis can include utilizing X-ray micro-CT to obtain multiple two-dimensional cross-sectional images of the foam and fiber composite throughout the foam and fiber composite's 10 total height 12. Acquiring a two-dimensional cross-sectional image of the foam and fiber composite 10 can provide for an analysis as to the extent of the insertion of the fibers 32 into the foam material 20 as well as the proportion of the fibers 32 to foam material 20 in the two-dimensional cross-sectional image. The two-dimensional cross-sectional image, obtained utilizing the X-ray micro CT, captures the structure of the foam and fiber composite 10 throughout the total height 12 of the foam and fiber composite 10 at known intervals throughout the total height 12 of the foam and fiber composite 10. From the two-dimensional cross-sectional image of the foam and fiber composite 10, the percentage of foam material 20 and the percentage of fiber 32 in various planes of the height 12, or sub-height 14, dimension of the foam and fiber composite 20 can be calculated. In various embodiments, the percentage of fibers 32 present in a plane of the foam and fiber composite 10 as measured through the sub-height 14 of the foam and fiber composite 10 can be from about 15 to about 25%. For example, a foam and fiber composite 10 can be subjected to X-ray micro-CT wherein a two-dimensional cross-sectional image can be been taken of the foam and fiber composite 10. Within the two-dimension cross-sectional image of the foam and fiber composite 10, the foam and fiber composite 10 sub-height 14 dimension can be evenly divided into thirds to provide three planar segments within the sub-height 14 of the foam and fiber composite 10. In such an example, each planar segment of the foam and fiber composite 10 manufactured according to the process described herein can demonstrate that a foam and fiber composite 10 of the disclosure herein can have fiber content from about 15% to about 25% in each one-third planar segment of the foam and fiber composite 10. The method utilized to measure the percentage of fibers 32 present in a foam material 20 as described in this example is described herein below.

As described herein, the foam and fiber composite 10 is formed by fluid inserting fibers 32 from a fibrous material 30 into an open cell foam material 20. The open cell foam material 20, by itself, can have permeability to air flow, as measured by a Frazier Differential Pressure Air Permeability Instrument. The permeability to air flow can be measured utilizing a Frazier 2000 model and following ASTM D 737-75. Typically, fluid inserting fibers 32 into an open cell foam material 20 will occlude the open cells and decrease the permeability to air flow of the foam material 20. It has been found that a foam material 20 which has fibers 32 fluid inserted into its open cells 26 according to the process described herein will have a permeability to air flow that is greater than the permeability of the open cell foam material 20 by itself. In various embodiments, open cell foam material 20 will have permeability to air flow of less than 200 CFM and the foam and fiber composite 10 will have permeability to air flow of greater than 300, 325, 350, or 375 CFM.

The foam and fiber composite 10 can have a total basis weight from about 20 gsm to about 250 gsm. The amount of fibrous material 30, including fibers 32 which have been inserted into the foam material 20, is at least about 10% of the total basis weight of the foam and fiber composite 10. In various embodiments, at least about 2, 5, 10, 15, 20, 30, 40, 50, 60 or 70 gsm of fibrous material 30 is brought into contact with a planar surface, such as planar surface 22, of the foam material 20.

Figure 2:
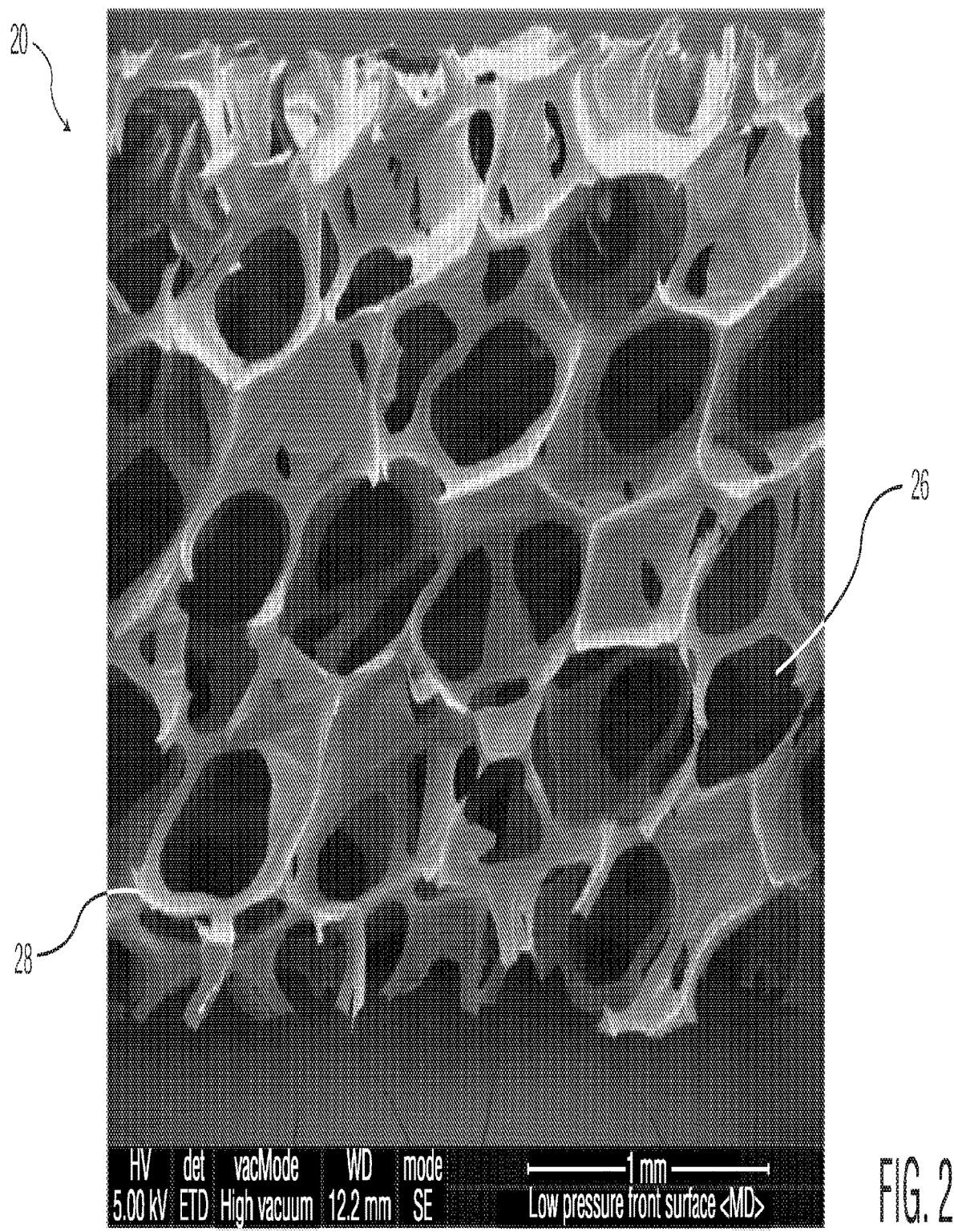
FIG. 2 is a photomicrograph of a cross-sectional view of a portion of an open cell foam material such that both planar surfaces are visible to the viewer.

FIG. 2 provides a photomicrograph of a cross-sectional view of a portion of an open cell foam material 20 such that both planar surfaces of the foam material 20 are visible to the viewer. The photomicrograph was taken by scanning electron microscope at a magnification of 40×. The foam material 20 can have a plurality of open cells 26 which are separated from each other by cell struts 28.

In various embodiments, the foam material 20 can be a flexible open cell foam such as polyester polyurethane foams, polyolefin foams, poly(styrene-butadiene) foams, or poly(ethylene-vinyl acetate) foams. In various embodiments, the foam material 20 is formed of polyester polyurethane. In various embodiments, the foam material 20 is hydrophobic. While the foam material 20 can be hydrophilic, it has been found that a hydrophobic foam material 20 can reduce and/or eliminate the migration of body exudates back to the topsheet layer of an absorbent article and can, therefore, reduce and/or eliminate the amount of body exudate at the topsheet layer of the absorbent article as well as the feel of wetness at the topsheet layer of the absorbent article.

Foam material 20 found suitable for use in a foam and fiber composite will have certain properties. The foam material 20 should be soft and flexible for its ultimate usage such as, for example, as a component of a foam and fiber composite in an absorbent article while also being able to withstand the fluid insertion manufacturing process. The properties which have been found to be beneficial for the foam material 20 provide for a foam material 20 that can withstand the pressures of the fluid insertion of the fibers from the fibrous material and can remain soft and flexible for use in a foam and fiber composite in an absorbent article.

The number of open cells 26 in the foam material 20 can provide the foam material 20 with measurement of the foam material's 20 porosity. The porosity of the foam material 20 is measured in pores per linear inch (ppi) and refers to the number of pores in one linear inch of a two-dimensional planar foam material surface and is described by the Polyurethane Foam Association. The pores per linear inch is measured by counting the pores visually under a microscope using a grid. The smaller the ppi value of the foam material 20 the larger the pore size, and vice versa. In various embodiments, the foam material 20 can have a porosity of from about 20 or 40 ppi to about 55, 65, or 90 ppi. It has been found that such porosities of the foam material 20 can allow for the utilization of lower fluid jet pressures during the fluid insertion manufacturing process. Lower fluid jet pressures during the fluid insertion process is beneficial as the structure of the foam material 20 can be maintained. The cell struts 28 of the foam material 20 can remain intact and permanent deformation of the foam material 20 can be avoided. Foam materials having porosities higher than 90 ppi can require higher fluid jet pressure during the fluid insertion process which can break the cell struts 28 of the foam material 20 and can permanently deform the foam material 20. Foam materials having porosities lower than 20 ppi are foam materials with cells of such a larger size dimension that the fibers from the fibrous material will not remain within the foam material during the fluid insertion process as such fibers will simply pass through the cells and out of the foam material.

In general, foam materials are capable of stretching. As foam materials in general are capable of stretching the foam material 20 can be negatively impacted by the fluid insertion manufacturing process in that the foam material 20 may be unduly stretched during the manufacturing process. The stretching of the foam material 20 can result in a foam material 20 having cells 26 which present in an elongated geometry rather than a more round or hexagonal geometry. Such an elongated geometry of the cells 26 can interfere with the fluid flow and insertion of the fibers during the fluid insertion manufacturing process. In various embodiments, it is beneficial if the foam material 20 has a reduced elongation capability. In various embodiments, the foam material 20 has a low elongation such as, for example, less than a 200% elongation at break. In various embodiments, the foam material 20 has an elongation at break from about 80 or 100% to about 150 or 200%.

In various embodiments, the foam material 20 can have a low density wherein the density of the foam material 20 can range from about 0.01 to about 0.08 g/cc. The foam material 20 should also have a certain compression modulus. For use in an absorbent article, it is desirable that the resultant foam and fiber composite 10 be soft and flexible. The foam material 20, however, must be able to withstand the compressive forces which are exerted during the fluid insertion process wherein fibers from a fibrous material are inserted into the foam material 20. If the foam material 20 is not able to withstand the compressive forces of the fluid insertion process, permanent deformation of the foam material 20 can result. In various embodiments, it has been found that a foam material 20 having a compression force deflection at 25% deflection from about 0.5 or 0.6 psi to about 0.8 or 1.0 psi will be able to balance the desire for a soft and flexible foam material 20 that can withstand the compressive forces of the fluid insertion process.

Figure 3:
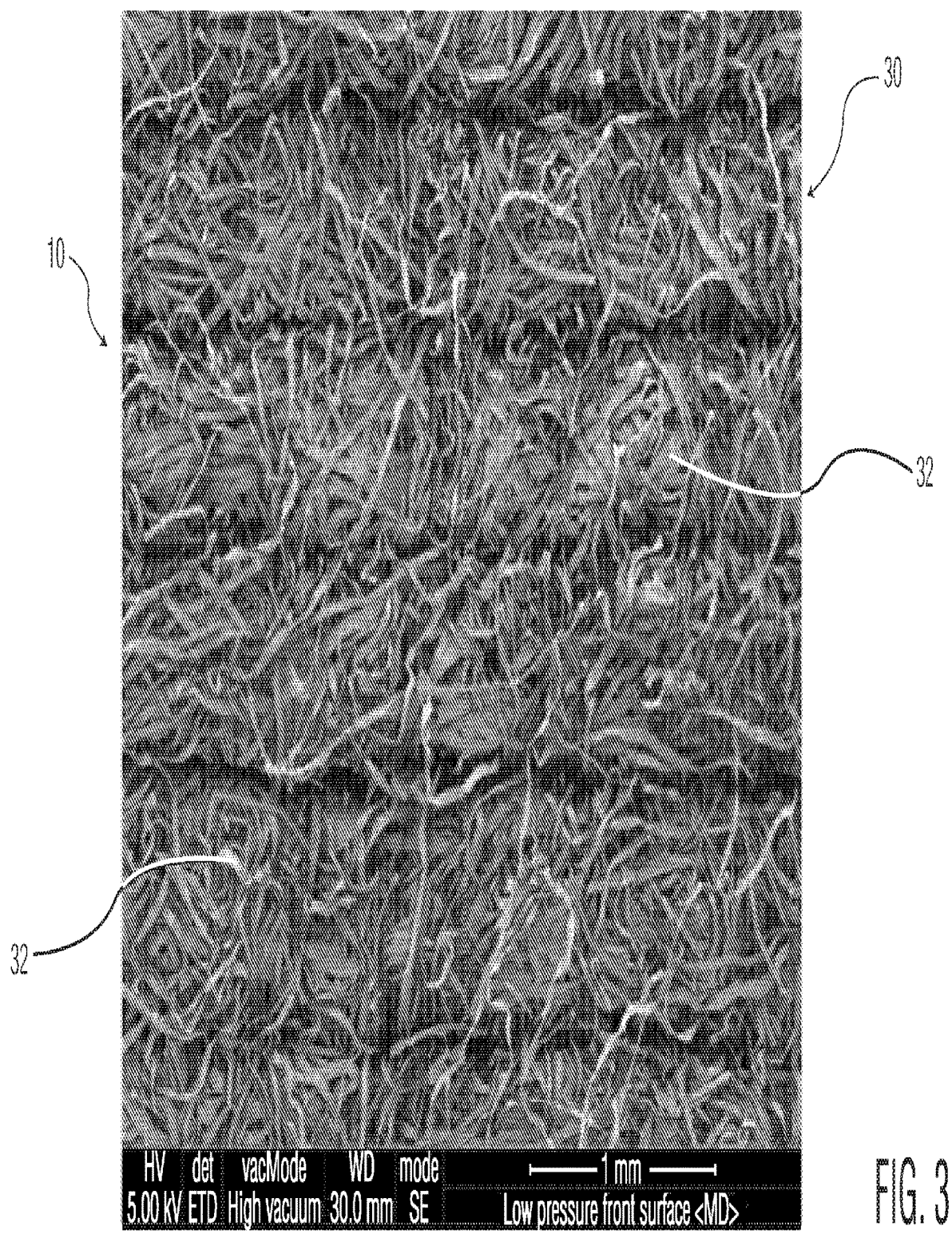
FIG. 3 is a photomicrograph of a planar view of the foam and fiber composite of FIG. 1 such that the fibrous material is visible to the viewer.
Figure 4:
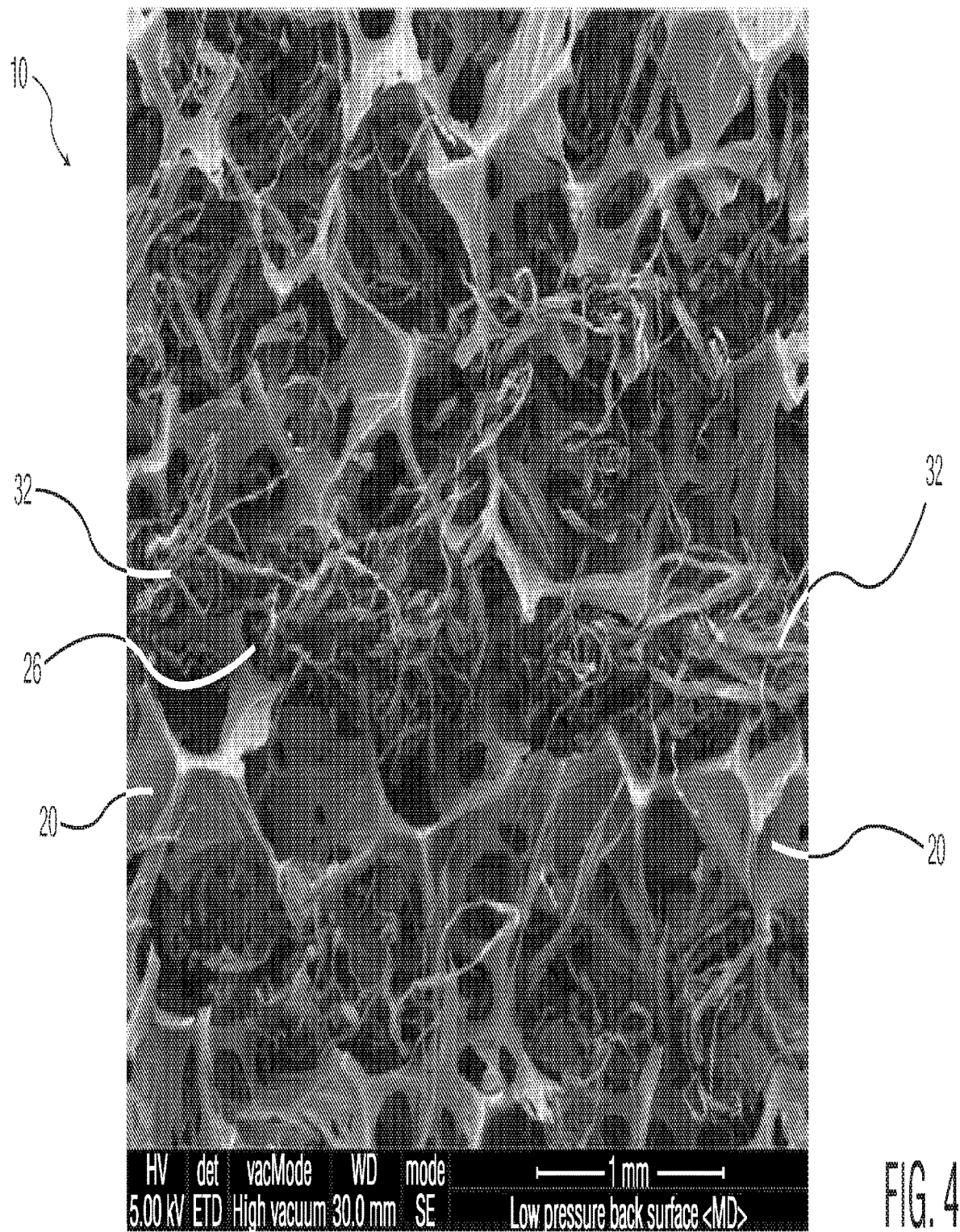
FIG. 4 is a photomicrograph of a planar view of the foam and fiber composite of FIG. 1 such that the second planar surface of the foam material and portions of fibers are visible to the viewer.

FIG. 3 provides a photomicrograph of a planar view of the foam and fiber composite 10 of FIG. 1 such that the fibrous material 30 is visible to the viewer. The photomicrograph was taken by scanning electron microscope at a magnification of 40×. As can be seen in FIG. 3, a fibrous material 30 composed of a plurality of individual fibers 32 covers the first planar surface 22 of the foam material 20. FIG. 4 provides a photomicrograph of a planar view of the foam and fiber composite 10 of FIG. 1 such that the second planar surface of the foam material 20 and portions of the fibers 32 are visible to the viewer. The photomicrograph was taken by scanning electron microscope at a magnification of 40×. As can be seen in FIG. 4, fibers 32 extend through the cells 26 of the foam material 20. Thus, with reference to FIGS. 1-4, a foam and fiber composite 10 can have a foam material 20 which can have a pair of opposing planar surfaces, 22 and 24, and a fibrous material 30 which can be brought into contact with one of the planar surfaces, such as planar surface 22, wherein a portion of the fibers 32 within the fibrous material 30 can be fluid inserted into the foam material 20 such that the fibers 32 can be present at both planar surfaces, 22 and 24, of the foam material 20 as well as extend through the cells 26 of the foam material 20.

In various embodiments, the fibrous material 30 can be formed from a plurality of individual fibers 32. In various embodiments, the individual fibers 32 of the fibrous material 30 can be a loose configuration such as may occur with wet-laying or air-laying of the fibrous material 30. In various embodiments, the individual fibers 32 of the fibrous material 30 can be in the form of a nonwoven web of material such as, for example, a carded nonwoven web. The fibrous material 30 can, therefore, be manufactured via various processes such as, but not limited to, air-laying, wet-laying, and carding. In various embodiments, the fibers 32 forming the fibrous material 30 can be hydrophilic. The fibers 32 forming the fibrous material 30 can be naturally hydrophilic or can be fibers which are naturally hydrophobic but which have been treated to be hydrophilic, such as, for example, via a treatment with a surfactant. Providing hydrophilic fibers 32 can allow for a foam and fiber composite 10 which can have hydrophilic pathways through the foam material 20. In various embodiments in which the foam material 20 is hydrophobic, the hydrophilic pathways provided by the hydrophilic fibers 32 can allow for the foam and fiber composite 10 in an absorbent article to intake bodily exudates (via the hydrophilic fiber pathways) and maintain the bodily exudates in a location away from the topsheet layer of the absorbent article as the bodily exudates will not be able to readily pass through the hydrophobic foam material 20. In various embodiments, the fibers 32 forming the fibrous material 30 can be cellulosic fibers such as, but not limited to, cotton, ramie, jute, hemp, flax, bagasse, northern softwood kraft pulp, as well as synthetic cellulosic fibers such as, but not limited to, rayon, viscose, and cellulosic acetate. In various embodiments, the fibers 32 forming the fibrous material 30 can be synthetic fibers made from polymers such as polyethylene, polypropylene, aromatic polyesters, aliphatic polyesters, and polyamides. In such embodiments, the fibers 32 can be treated with additives to impart various degrees of surface energy ranging from very low surface energy and low wettability to high surface energy and high wettability.

The fibrous material 30 in contact with a planar surface of the foam material 20, such as, for example, the first planar surface 22 of the foam material 20, can have a density from about 0.08 g/cc to about 2.0 g/cc. In calculating the density of the fibrous material 30, only the portion of the fibrous material 30 external to the foam material 20 is considered. The portions of fibers 32 of the fibrous material 30 which have been inserted into the foam material 20 and, therefore, extend into and/or through the foam material 20 are not included when calculating the density of the fibrous material 30.

Fluid Insertion Manufacturing Process:

To form the foam and fiber composite 10 of the current disclosure, a fluid insertion manufacturing process can be utilized. Any number of fluids can be used to form the foam and fiber composite 10, including both liquids and gases. In various embodiments, pressurized water is used as the fluid for fiber insertion.

Figure 5:
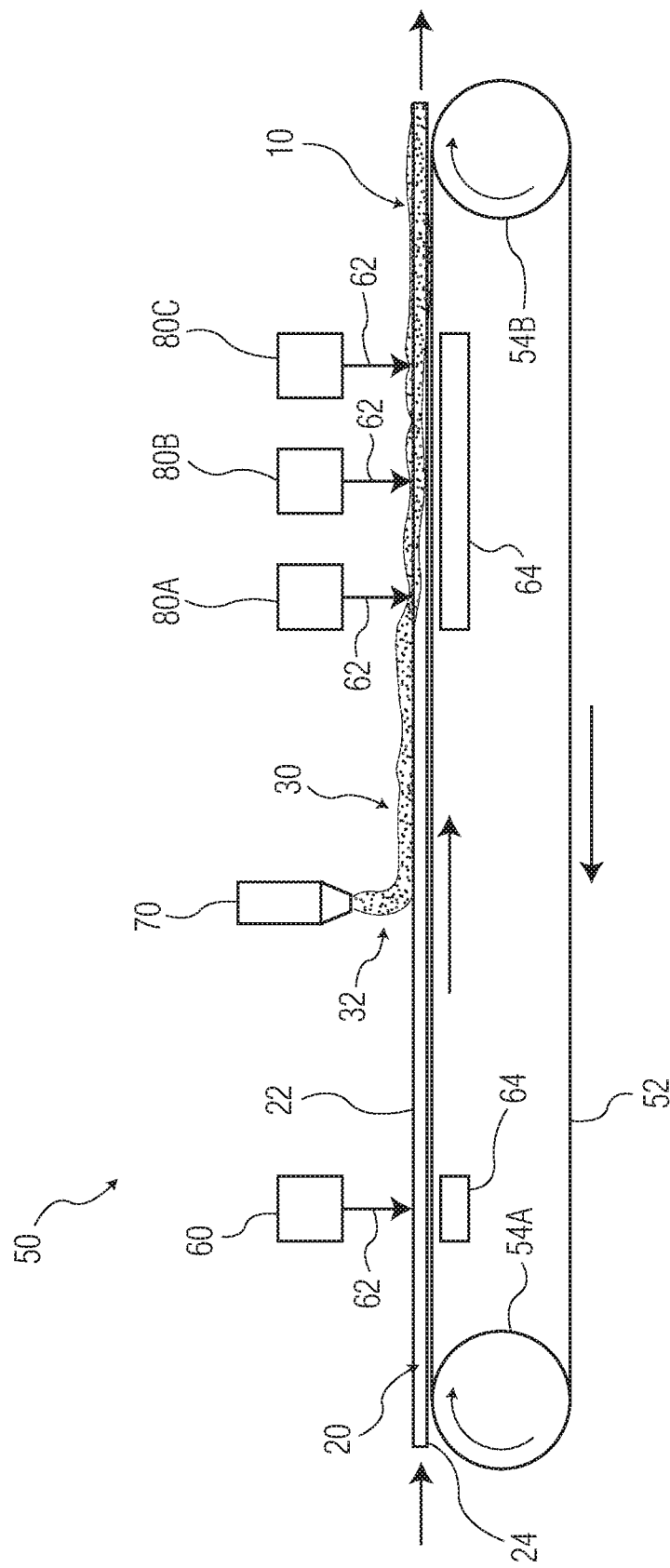
FIG. 5 is a schematic illustration of an exemplary process of a fluid insertion process to insert fibers from a fibrous material into an open cell foam material.

FIG. 5 illustrates an example of a fluid insertion process 50 which can be utilized to form the foam and fiber composite 10. In the example illustrated in FIG. 5, a foam material 20 is supported on a support belt 52. The support belt 52 can be supported on two or more rolls, 54A and 54B, which are provided with a suitable driving means (not shown) for moving the support belt 52 forward, generally in the machine direction, continuously. The support belt 52 may be, for example, a single plain weave foraminous wire. The support belt 52 should be fluid pervious to allow the fluid 62 to pass through the foam material 20 and the support belt 52. The support belt 52 should have a mesh size providing large openings between the wires forming the support belt 52. In various embodiments, the openings of the support belt 52 can be provided as a measurement of the percent open area and the support belt 52 can have a percent open area of greater than about 10, 12, 14, 16, 18 or 20%. The large mesh size can enable the fluid utilized during the fluid insertion manufacturing process 50 to pass through the support belt 52 rather than rebound off the support belt 52 and back into the foam material 20. Allowing the fluid to rebound into the foam material 20 may result in the application of a return pressure on the fibers 32 of the fibrous material 30 which can result in the fibers 32 being pushed back through the foam material 20. In the current disclosure, allowing the fluid to pass through the support belt 52 can enable the fibers 32 of the fibrous material 30 to be inserted into the foam material 20 during the fluid insertion manufacturing process 50 and extend from the first planar surface 22 to the second planar surface 24 of the foam material 20.

As described herein, foam materials are capable of stretching. As foam materials in general are capable of stretching the foam material 20 can be negatively impacted by the fluid insertion manufacturing process 50 in that the foam material 20 may be unduly stretched during the manufacturing process 50. The stretching of the foam material 20 can result in a foam material 20 having cells 26 which present in an elongated geometry rather than a more round or hexagonal geometry. Such an elongated geometry of the cells 26 can interfere with the fluid flow and insertion of the fibers 32 during the fluid insertion manufacturing process 50. In various embodiments, it is beneficial to maintain the strain rate on the foam material 20 at less than about 2 or 5% strain during the fluid insertion manufacturing process 50.

Figure 6:
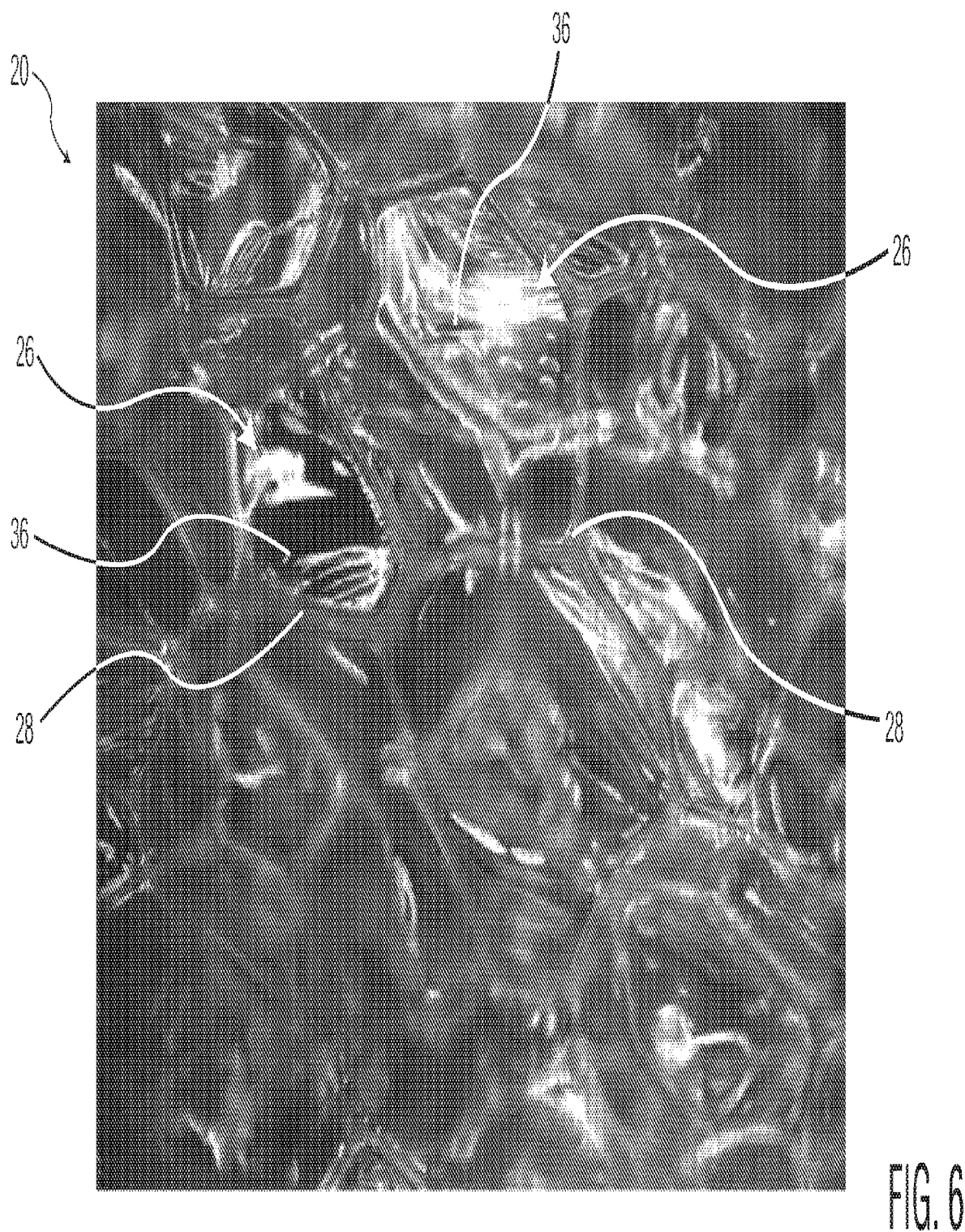
FIG. 6 is a photomicrograph of a portion of a foam material prior to pre-treatment.
Figure 7:
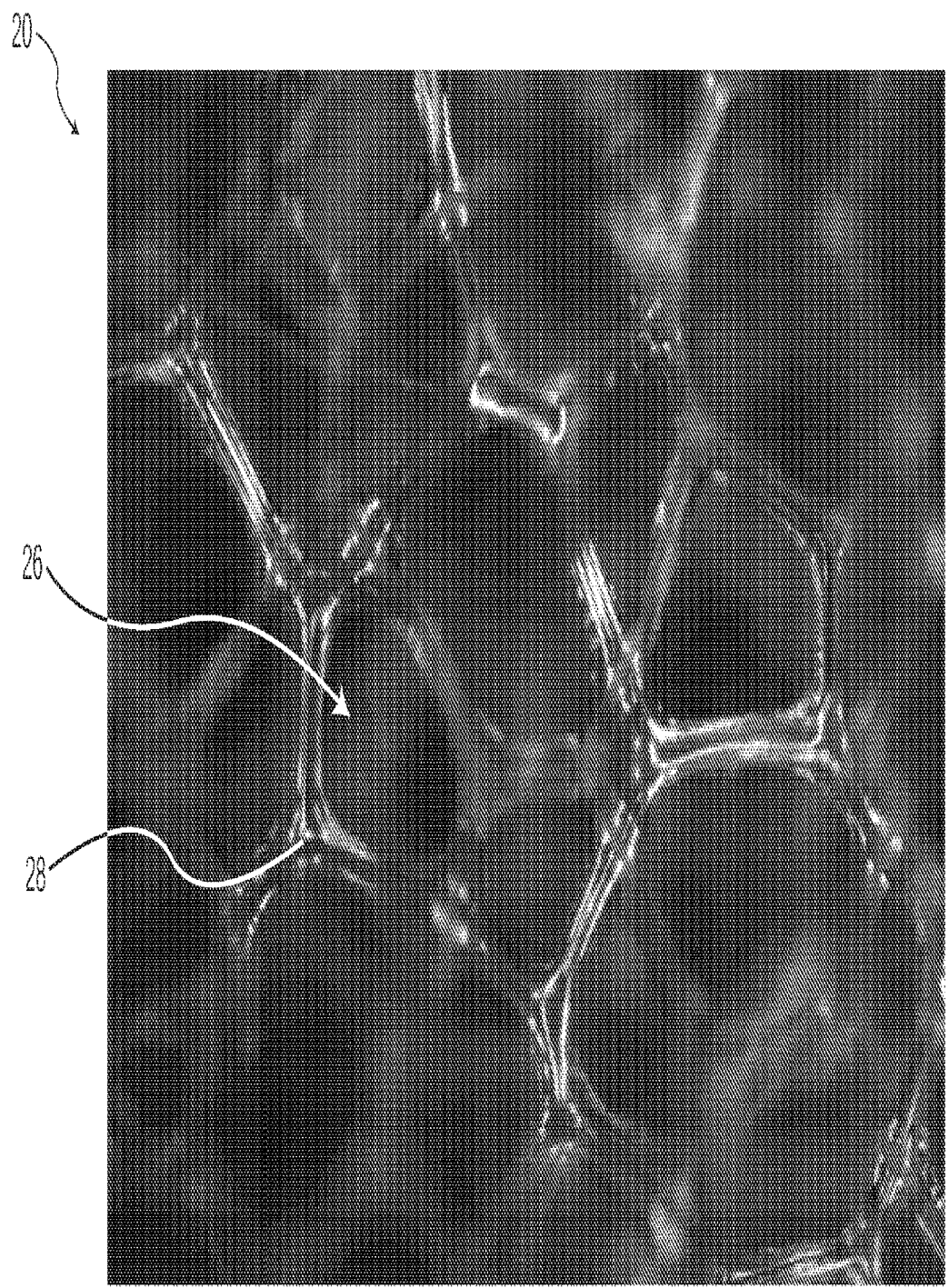
FIG. 7 is a photomicrograph of a portion of a foam material after pre-treatment.

The foam material 20 is supplied to the fluid insertion manufacturing process 50 via the support belt 52. In the fluid insertion manufacturing process 50 illustrated in FIG. 5, the foam material 20 can undergo a pre-treatment phase prior to a fluid insertion phase. FIG. 6 provides a photomicrograph of a portion of a foam material 20 prior to pre-treatment. The photomicrograph was taken by an optical stereo microscope. As can be seen in FIG. 6, prior to the pre-treatment of the foam material 20, the foam material 20 can have cells 26 which are separated from each other by struts 28. Spanning each of the cells 26 is a cell membrane 36. The presence of the cell membranes 36 can inhibit the movement of fibers 32 through the foam material 20. The pre-treatment of the foam material 20 can break the cell membranes 36 increasing the ability of the fibers 32 to move through the foam material 20 during the fluid insertion phase of the fluid insertion manufacturing process 50. To pre-treat the foam material 20, a fluid treatment device 60 can be spaced above the foam material 20. As the foam material 20 passes below the fluid treatment device 60 a stream of fluid 62 can emanate from the fluid treatment device 60 and impinge upon the foam material 20. The fluid 62 impinging upon the foam material 20 can cause the cell membranes 36 within the foam material 20 to rupture. The fluid pressure from the fluid treatment device 60 is generally in the range of from about 150, 200, 250, 300, 350, 400, 450, or 500 psi to about 550, 600, 650, 700, 750, 800, 850, 900, 950, or 1000 psi. The fluid pressure during the pre-treatment phase of the fluid insertion manufacturing process 50 described herein is low enough to rupture the cell membranes 36 which span the cells 26 of the foam material 20 without also rupturing the struts 28 of the foam material 20. Utilizing a fluid pressure greater than 1000 psi can rupture the struts 28 of the foam material 20 which can result in permanent deformation of the foam material 20. In addition to rupturing the cell membranes 36 pre-treatment of the foam material 20 can also increase the permeability to air flow of the foam material 20. In various embodiments, the foam material 20 has a permeability to air flow of less than about 200 CFM prior to pre-treatment and a permeability to air flow of greater than about 600 CFM after pre-treatment. FIG. 7 provides a photomicrograph of a portion of a foam material 20 following pre-treatment. The photomicrograph was taken by an optical stereo microscope. As can be seen in FIG. 7, following the pre-treatment phase of the fluid insertion manufacturing process 50, the foam material 20 can have cells 26 which are separated by struts 28. The cell membranes 36 have been ruptured by the pre-treatment phase and are not visible in FIG. 7.

In FIG. 5 a single fluid treatment device 60 is shown, however, multiple fluid treatment devices 60 can be utilized. The fluid treatment device 60 can have a single pressurized fluid jet or a plurality of pressurized fluid jets. The fluid 62 of the fluid treatment device 60 can emanate from injectors via jet packs or strips (not shown) consisting of a row or rows of pressurized fluid jets with small apertures of a diameter usually between 0.08 and 0.15 mm and spacing of around 0.5 mm in the cross-machine direction. As the jet packs or strips are oriented in a jet pattern of a row or rows of pressurized fluid jets, this jet pattern will result in a pattern of fluid treatment on the foam material 10 of a row or rows which correspond to the jet pattern. Other jet sizes, spacings, jet patterns, and number of jets can be used. In various embodiments, it may be deemed suitable to pre-treat the foam material 20 by directing the fluid emanating from the fluid treatment devices 60 towards the foam material 20 in a pattern such as, but not limited to, rows, columns, swirls, circles, dots, squares, ovals, triangles, diamonds, etc. In various embodiments, a mask may be placed over the foam material 20 and the mask may be a solid material such as, for example, a film sheet or a metal sheet, with holes cut therethrough. The holes can allow for passage of fluid emanating from the pressurized fluid jet(s). The fluid that passes through the holes of the mask can treat the foam material 20 such that the foam material 20 can a discontinuous treatment which will correspond to the pattern of the location of the holes in the mask. In various embodiments, the mask may be a solid material, such as, for example, a film sheet or a metal sheet, with a continuous pattern cut therethrough. A non-limiting example of a continuous pattern is a honeycomb pattern in which the cut away portions of the mask surround portions of the mask which remain. It is to be understood that in such an example in order to maintain the centers of the honeycomb within the material of the mask, the cut away portions of the mask are not completely cut away but small connecting segments remain to maintain the mask material in place in the center of the honeycomb and to maintain the stability of that material. The fluid that passes through the cut away portions of the mask can treat the foam material 20 in a continuous pattern that will correspond to the pattern of the cut away material of the mask. The fluid treatment device 60 will typically have the jet orifices spaced from about 5 to about 20 mm from the surface of the foam material 20, though the spacing can vary depending on the basis weight of the foam material 20, the fluid pressure, the number of individual jets being used, the amount of vacuum being used via the removal system 64 and the speed at which the support belt 52 is being run. The jets can also be of the type where the direction, volumetric flow, and pressure can be varied continuously or intermittently to create various patterns of fluid treatment of the foam material 20. To remove the fluid 62 emanating from the fluid treatment device 60 a removal system 64 such as a vacuum or other conventional fluid removal system can be used below the support belt 52.

Figure 8:
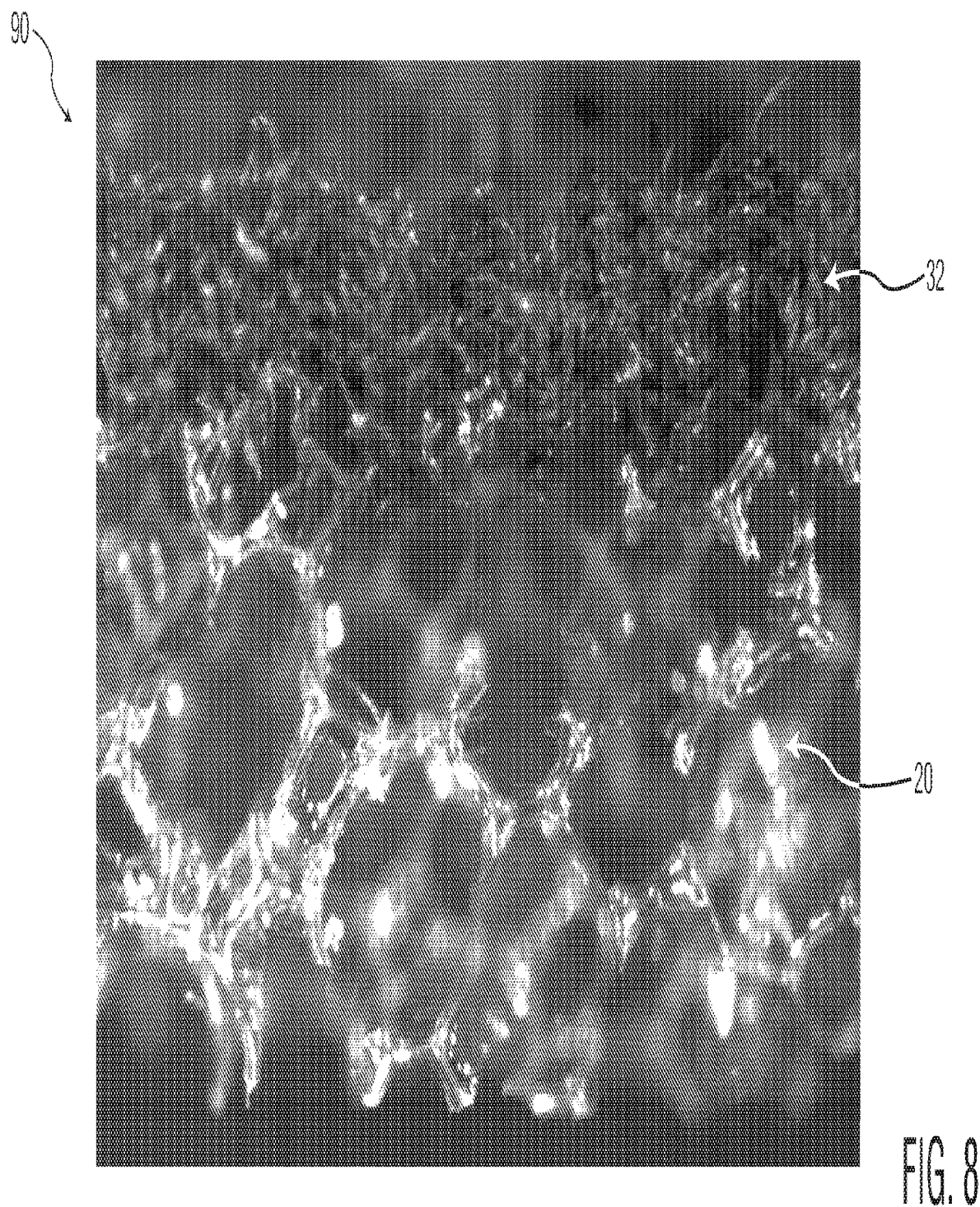
FIG. 8 is a photomicrograph of a portion of a foam material in contact with a fibrous material.

Following the pre-treatment phase of the fluid insertion manufacturing process 50 a fibrous material 30 can be brought into contact with the pre-treated foam material 20. The fibrous material 30 can be formed of individual fibers 32 and/or a nonwoven web of material formed of individual fibers 32 and the fibrous material 30 can be provided via a fibrous material source 70. In various embodiments, the fibrous material source 70 can be positioned above the foam material 20 and the fibrous material 30 can be airlaid or wetlaid onto the foam material 20. In various embodiments, the fibrous material source 70 can a web material source and can provide the fibrous material 30 as a carded nonwoven web. FIG. 8 provides a photomicrograph of a fibrous material 30 which has been brought into contact with the foam material 20. The photomicrograph was taken by an optical stereo microscope. As can be seen in FIG. 8, a layered composite 90 of the foam material 20 and the fibrous material 30 can be formed due to the deposition of the fibrous material 30 onto one of the planar surfaces of the foam material 20. The fibrous material 30 being deposited onto the planar surface of the foam material 20 is an unbonded or relatively unbonded material such that the individual fibers 32 forming the fibrous material 30 can move in a three-dimensional manner (in each of the X-, Y-, and Z-directions) in relation to each other individual fiber present in the fibrous material 30. The foam material 20, in a top down view, can have a length dimension and a width dimension. In various embodiments, the fibrous material 30 being deposited onto the planar surface of the foam material 20 can be deposited such that the fibrous material 30 can fully cover the length dimension and the width dimension of the foam material 20. In various embodiments, the fibrous material 30 can be deposited such that the fibrous material 30 can cover less than the full length dimension, less than the full width dimension, or less than each of the full length and full width dimensions of the foam material 20. For example, in various embodiments, the deposition of the fibrous material 30 onto the planar surface of the foam material 20 can be intermittent in the length dimension, i.e., the machine direction, of the foam material 20, the deposition of the fibrous material 30 onto the planar surface of the foam material 20 can be intermittent in the width dimension, i.e., the cross-machine direction, of the foam material 20, or the deposition of the fibrous material 20 onto the planar surface of the foam material 20 can be intermittent in each of the length dimension and width dimension, i.e., the machine direction and the cross-machine direction, of the foam material 20. In various embodiments, the fibrous material 30 can be deposited onto a planar surface of the foam material 20 in any pattern as deemed suitable including, but not limited to, rows, columns, swirls, circles, dots, squares, ovals, triangles, diamonds, etc.

The layered composite 90 of the foam material 20 and the fibrous material 30 is then passed under at least one fluid insertion device 80. In various embodiments, the fluid pressures can range from about 70, 80, 90, 100, 125, 150, 175, 200, 225, 250, or 275 psi to about 300, 350, 400, 450, 500, 550, 600, 650, 700, 750, 800, 850, 900, 950, or 1000 psi. FIG. 5 illustrates the usage of three fluid insertion devices, 80A, 80B, and 80C. When multiple fluid insertion devices are utilized the fluid pressure in each subsequent fluid insertion device can be higher than the preceding fluid insertion device so that the energy imparted to the composite increases and the insertion of the fibers 32 from the fibrous material 30 increases. This reduces disruption of the overall evenness of the areal density of the foam and fiber composite 10 by the pressured fluid jets while achieving the desired level of fluid insertion of the fibers 32 from the fibrous material 30. In various embodiments, such as, for example, the exemplary embodiment illustrated in FIG. 5 wherein three fluid insertion devices, 80A, 80B, and 80C, are utilized, the fluid pressure of fluid insertion device 80A can be 72.5 psi, the fluid pressure of fluid insertion device 80B can be 145 psi, and the fluid pressure of fluid insertion device 80C can be 290 psi. The fluid insertion device 80 can have a single pressurized fluid jet or a plurality of pressurized fluid jets. The fluid 62 of the fluid insertion device 80 can emanate from injectors via jet packs or strips (not shown) consisting of a row or rows of pressurized fluid jets with small apertures of a diameter usually between 0.08 and 0.15 mm and spacing of around 0.5 mm in the cross-machine direction. As the jet packs or strips are oriented in a jet pattern of a row or rows of pressurized fluid jets, this jet pattern will result in a pattern of fluid insertion of the fibers 32 into the foam material 10 of a row or rows which correspond to the jet pattern. Other jet sizes, spacings, jet patterns, and number of jets can be used. The fluid insertion device 80 will typically have the jet orifices spaced from about 5 to about 20 mm from the surface of the composite of layers, though the spacing can vary depending on the basis weight of the composite of layers, the fluid pressure, the number of individual jets being used, the amount of vacuum being used via the removal system 64 and the speed at which the support belt 52 is being run. In various embodiments the jets can be oriented such that the fluid emanating from the jets is perpendicular to the layered composite 90. In various embodiments, the jets can be oriented such that the fluid emanating from the jets is at an angle to the layered composite 90. In various embodiments, a portion of jets can be oriented such that the fluid emanates in a direction perpendicular to the layered composite 90 and a portion of jets can be oriented such that the fluid emanates from the jets at angle to the layered composite 90. The jets can also be of the type where the direction, volumetric flow, and pressure can be varied continuously or intermittently to create various patterns of fluid insertion of the fibers 32 into the foam material 20. To remove the fluid 62 emanating from the fluid insertion device 80 a removal system 64 such as a vacuum or other conventional fluid removal system can be used below the support belt 52.

Figure 9:
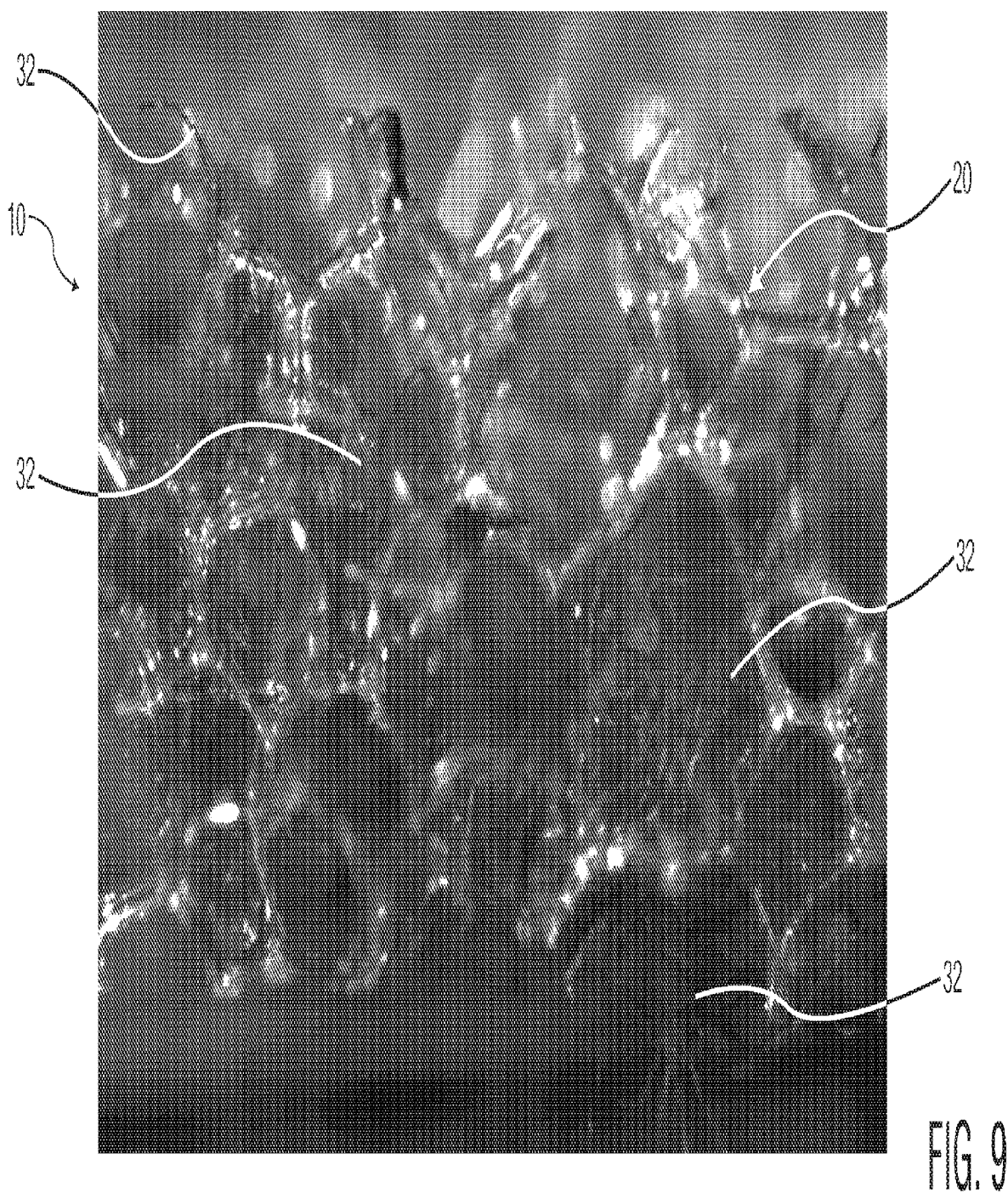
FIG. 9 is a photomicrograph of a portion of a foam and fiber composite.

The fluid 62 emanating from the fluid insertion device 80 can promote movement of some of the individual fibers 32 from the fibrous material 30 into and through the foam material 20. The fibrous material 30 is unbonded or relatively bonded. Each individual fiber 32 can move in a three-dimensional manner (in each of the X-, Y-, and Z-directions) with regard to each other individual fiber 32 that forms the fibrous material 30. The fluid 62 emanating from the fluid insertion device 80 can cause the fibers 32 to move and that movement can include movement into and through the foam material 20. The net result of this movement of fibers 32 is the creation of the foam and fiber composite 10. FIG. 9 provides a photomicrograph of a foam and fiber composite 10. The photomicrograph was taken by an optical stereo microscope. As can be seen in FIG. 9, individual fibers 32 have moved through the foam material 20 and extend through the foam material 20.

As described herein, the fiber insertion manufacturing process 50 can include a single fiber insertion device 80 or multiple fiber insertion devices such as, 80A, 80B, and 80C. A fiber insertion device 80 can have at least one pressurized fluid jet which can emit a pressurized fluid towards the fibrous material 30 and the foam material 20. In various embodiments, the at least one pressurized fluid jet is not stationary and can move in the machine direction and/or cross-machine direction. Such movement can create any of a variety of patterns of fiber insertion as deemed suitable. Such patterns can include, but are not limited to, rows, swirls, circles, dots, squares, ovals, triangles, diamonds, etc. In various embodiments, the pattern can be continuous. In various embodiments, the pattern can be discontinuous. In various embodiments, the pressure of the pressurized fluid emitted from the pressurized fluid jet can vary. Such variance in pressure of fluid emitted from the jet can result in fibers 32 being inserted into and through the foam material 20 at different heights of the sub-height 14 of the foam material 20 of the foam and fiber composite 10. For example, some fibers 32 may remain closer to the first planar surface 22 of the foam material 20, some fibers 32 may extend into the middle of the foam material 20, and some fibers 32 may reach to the second planar surface 24 of the foam material 20. In various embodiments, the fiber insertion device 80 can have multiple pressurized fluid jets and each jet can vary in pressure from each other jet. Such variance in pressure between each fluid jet can result in fibers 32 being inserted into and through the foam material 20 at different heights of the sub-height 14 of the foam material 20 of the foam and fiber composite 10. In various embodiments, multiple fiber insertion devices can be utilized and the pressure of the fluid emitted from each fiber insertion device can vary from each other fluid insertion device. In various embodiments, a foam and fiber composite 10 can have at least one portion of the foam and fiber composite 10 which is free from the presence of fibers 32 within the foam material 20. For example, a foam material 20, when viewed from a top down perspective, can have a central region and opposing side edge regions. A fibrous material 30 can be brought into contact with the central region of the foam material 20 and subjected to the fiber insertion manufacturing process 50 described herein. The resultant foam and fiber composite 10 can have a central region having hydrophilic pathways through the foam material 20 and a pair of opposing side regions which are hydrophobic due to the lack of presence of fibers 32. In various embodiments, a fibrous material 30 which is hydrophilic can be brought into contact with the central region of the foam material 20 and a fibrous material 30 which is hydrophobic can be brought into contact with the side regions of the foam material 20. In such embodiments, each of the hydrophilic fibrous material 30 and the hydrophobic fibrous material 30 can be subjected to the fiber insertion manufacturing process 50 described herein. The resultant foam and fiber composite 10 can have a central region having hydrophilic pathways through the foam material 20 and a pair of opposing side regions which are hydrophobic due to the presence of hydrophobic fibers. As an additional example, a fibrous material 30 can be deposited onto a planar surface of a foam material 20 in a pattern such that the fibrous material 30 is deposited in columns which can extend in the length dimension, i.e., the machine direction, of the foam material 20 and space can be present between each column of fibrous material 30 in the width dimension, i.e., the cross-machine direction, of the foam material 20 where no fibrous material 30 is present. A resultant foam and fiber composite 10 can have alternating hydrophilic regions and hydrophobic regions. As described herein, the fibrous material 30 can be deposited onto the foam material 20 in any pattern deemed suitable which can result in a foam and fiber composite 10 having a corresponding pattern of hydrophilic regions and hydrophobic regions. The foam and fiber composite 10 can have a varying presence of fibers 32 through the foam material 20 of the foam and fiber composite 10 in the X-, Y-, and Z-directions of the foam material 20 of the foam and fiber composite 10.

In various embodiments, a fibrous material 30 can be deposited onto a planar surface of a foam material 20. In various embodiments, prior to fluid insertion of any of the fibers 32 from the fibrous material 30 into the foam material 20, a mask may be placed over the fibrous material 30. In various embodiments, the mask may be a solid material, such as, for example, a film sheet or a metal sheet, with holes cut therethrough. The holes can allow for the passage of the fluid emanating from the pressurized fluid jet(s). The fluid that passes through the holes of the mask can insert fibers 32 from the fibrous material 30 into the foam material 20. The resultant foam and fiber composite 10 can have discontinuous insertion of fibers 32 from the fibrous material 30 into the foam material 20 which will correspond with the location of the holes in the mask. In various embodiments, the mask may be a solid material, such as, for example, a film sheet or a metal sheet, with a continuous pattern cut therethrough. A non-limiting example of a continuous pattern is a honeycomb pattern in which the cut away portions of the mask surround portions of the mask which remain. It is to be understood that in such an example in order to maintain the centers of the honeycomb with the material of the mask, the cut away portions of the mask are not completely cut away but small connecting segments remain to maintain the mask material in place in the center of the honeycomb and to maintain the stability of that material. The fluid that passes through the cut away portions of the mask can insert fibers 32 from the fibrous material 30 into the foam material 20 in a continuous pattern that will correspond to the pattern of the cut away material of the mask.

In various embodiments, it may be desirable to deposit multiple layers of fibrous material 30 onto a planar surface of the foam material 20. In various embodiments, each layer of the fibrous material 30 can be hydrophilic. In various embodiments, each layer of the fibrous material 30 can be hydrophobic. In various embodiments, at least one layer of fibrous material 30 can be hydrophilic and at least one layer of fibrous material can be hydrophobic. In various embodiments, each layer of fibrous material 30 can undergo its own fiber insertion manufacturing process 50 such as described herein in a sequential process. In various embodiments, the multiple fibrous layers 30 can undergo a fiber insertion manufacturing process 50 such as described herein at the same time. In various embodiments, each layer of fibrous material 30 can be deposited in any pattern deemed suitable including, but not limited to, the deposition patterns described herein. In various embodiments, each layer of fibrous material 30 can have fibers inserted into the foam material 20 in any pattern deemed suitable including, but not limited to, the fiber insertion patterns described herein.

In various embodiments, the fluid treatment device 60 and the fluid insertion devices 80 are conventional fluid treatment devices the construction and operation of which are well known to those of ordinary skill in the art. See for example, U.S. Pat. No. 3,485,706 to Evans, the contents of which are incorporated herein by reference in its entirety to the extent it does not conflict with the information contained herein.

Absorbent Article:

An absorbent article which incorporates the foam and fiber composite 10 described herein can have improved dryness and an improved liquid distribution capability. An absorbent article can have a longitudinal direction, a transverse direction, and a depth direction. The absorbent article can have a topsheet layer, a backsheet layer, and an absorbent system positioned between the topsheet layer and the backsheet layer. The absorbent system can have at least a foam and fiber composite 10 such as described herein. The foam and fiber composite 10 can be positioned below the topsheet layer in the depth direction of the absorbent article. In various embodiments, the absorbent system can further include an absorbent core. In such embodiments, the absorbent core can be positioned below the foam and fiber composite 10 in the depth direction of the absorbent article. The foam and fiber composite 10 can be capable of fluid intake as well as distributing fluid in at least the longitudinal direction of the absorbent article.

Figure 10:
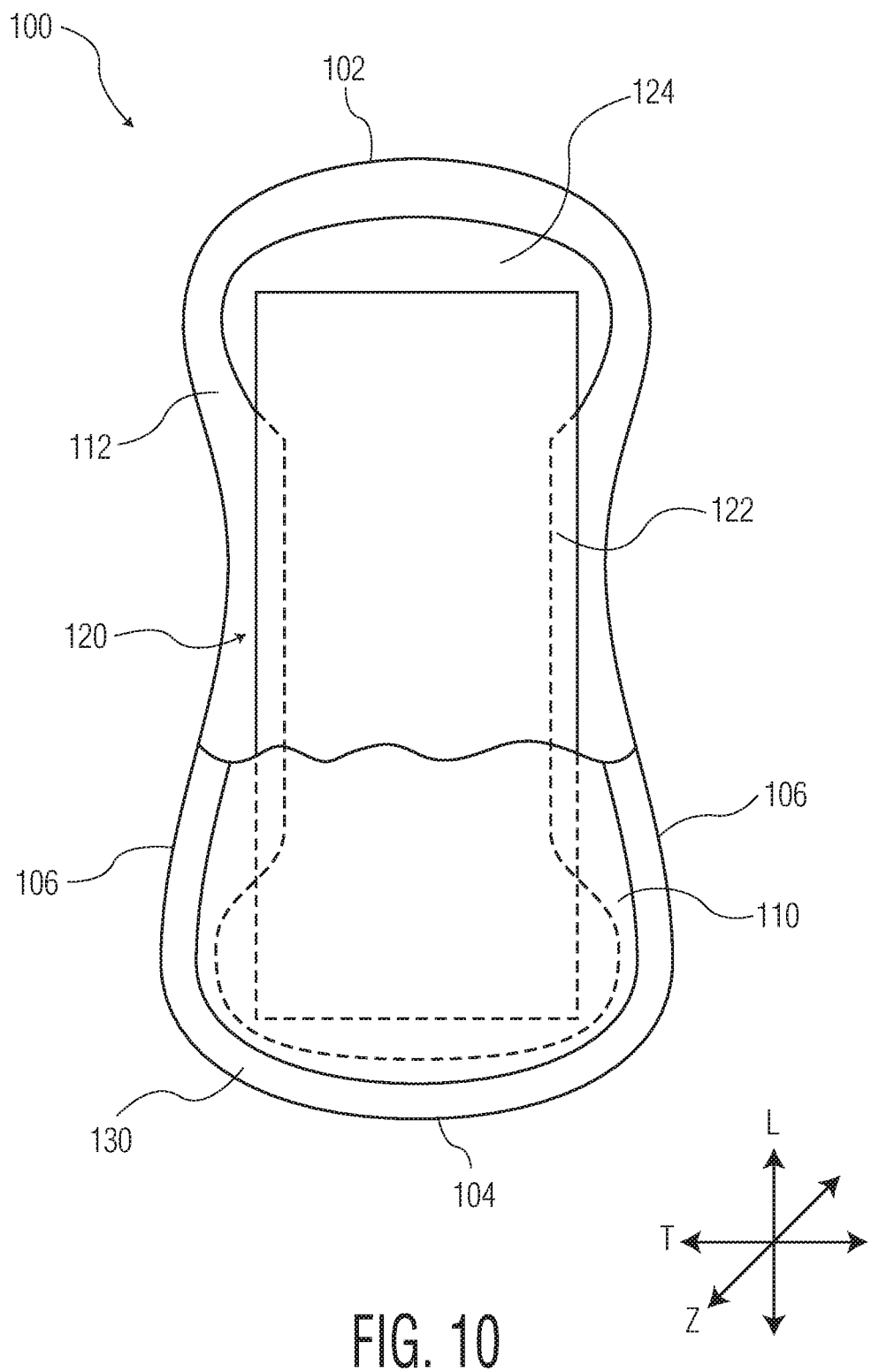
FIG. 10 is a top down view of an embodiment of an absorbent article with portions cut away to show underlying features.

Referring to FIG. 10, FIG. 10 provides an illustration of a top down view of an example of an absorbent article 100 such as a feminine pad. While elements of a feminine pad are illustrated and described herein it is to be understood that additional elements can be incorporated into the feminine pad, such as, but not limited to, additional layers of an absorbent system such as a fluid intake layer, distribution layer, surge layer, as well as additional components such as wings. It is further to be understood that the foam and fiber composite 10 described herein can be incorporated into a variety of absorbent articles, such as, but not limited to, feminine pads, sanitary napkins, panty shields, pantiliners, diapers, training pants, and incontinence devices.

Referring to FIG. 10, the absorbent article 100 can have a longitudinal direction (L), a transverse direction (T), and a depth direction (Z). The absorbent article 100 can have a first transverse direction end edge 102, a second transverse direction end edge 104 opposite the first transverse direction end edge 102, and a pair of opposing longitudinal direction side edges 106. In various embodiments, the absorbent article 100 can take on various geometries but will generally have a pair of opposing longitudinal direction side edges 106 and a pair of opposing transverse direction end edges 102 and 104. The absorbent article 100 can have a wearer facing, liquid permeable topsheet layer 110 and a garment facing, liquid impermeable backsheet layer 112. An absorbent system 120 can be positioned between the topsheet layer 110 and the backsheet layer 112. The absorbent system 120 can include an intake and distribution layer 122 and, in various embodiments, can further include an absorbent core 124.

The topsheet layer 110 and the backsheet layer 112 can both extend beyond the outermost peripheral edges of the absorbent system 120 and can be peripherally bonded together, either entirely or partially, using known bonding techniques to form a sealed peripheral region 130. For example, the topsheet layer 110 and the backsheet layer 112 can be bonded together by adhesive bonding, ultrasonic bonding, or any other suitable bonding method known in the art.

Each of these components of the absorbent article 100 will be described in more detail herein.

Topsheet Layer:

The topsheet layer 110 defines a wearer facing surface of the absorbent article 100 that may directly contact the body of the wearer and is liquid permeable to receive body exudates. The topsheet layer 110 is desirably provided for comfort and conformability and functions to direct body exudates away from the body of the wearer, through its own structure, and towards the absorbent system 120. The topsheet layer 110 desirably retains little to no liquid in its structure, so that it provides a relatively comfortable and non-irritating surface next to the skin of the wearer of the absorbent article 100.

The topsheet layer 110 can be a single layer of material, or alternatively, can be multiple layers that have been laminated together. The topsheet layer 110 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 110.

In various embodiments, the topsheet layer 110 can be constructed from various nonwoven webs such as meltblown webs, spunbond webs, hydroentangled spunlace webs, or through air bonded carded webs. Examples of suitable topsheet layer 110 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 110 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 110, each of which is hereby incorporated by reference thereto in its entirety. Additional topsheet layer 110 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 110 may contain a plurality of apertures (not shown) formed therethrough to permit body exudates to pass more readily into the absorbent system 120. The apertures may be randomly or uniformly arranged throughout the topsheet layer 110. The size, shape, diameter, and number of apertures may be varied to suit an absorbent article's 100 particular needs.

In various embodiments, the topsheet layer 110 can have a basis weight ranging from about 5, 10, 15, 20 or 25 gsm to about 50, 100, 120, 125 or 150 gsm. For example, in an embodiment, a topsheet layer 110 can be constructed from a through air bonded carded web having a basis weight ranging from about 15 gsm to about 100 gsm. In another example, a topsheet layer 110 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others.

In various embodiments, the topsheet layer 110 can be at least partially hydrophilic. In various embodiments, a portion of the topsheet layer 110 can be hydrophilic and a portion of the topsheet layer 110 can be hydrophobic. In various embodiments, the portions of the topsheet layer 110 which can be hydrophobic can be either an inherently hydrophobic material or can be a material treated with a hydrophobic coating.

In various embodiments, the topsheet layer 110 can be a multicomponent topsheet layer 110 such as by having two or more different nonwoven or film materials, with the different materials placed in separate locations in the transverse direction T of the absorbent article 100. For example, the topsheet layer 110 can be a two layer or multicomponent material having a central portion positioned along and straddling a longitudinal centerline of the absorbent article 100, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 110 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 110 can be positioned symmetrically about the absorbent article 100 longitudinal centerline. Such central longitudinally directed central portion can be a through air bonded carded web ("TABCW") having a basis weight between about 15 and about 100 gsm. Previously described nonwoven, woven, and apertured film topsheet layer materials may also be used as the central portion of a topsheet layer 110. In various embodiments, the central portion can be constructed from a TABCW material having a basis weight from about 20 to about 50 gsm such as is available from Xiamen Yanjan Industry, Beijing, DaYuan Nonwoven Fabrics, and others. Alternatively, apertured films, such as those available from such film suppliers as Texol, Italy and Tredegar, U.S.A. may be utilized. Different nonwoven, woven, or film sheet materials may be utilized as the side portions of the topsheet layer 110. The selection of such topsheet layer 110 materials can vary based upon the overall desired attributes of the topsheet layer 110. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 110 design, it may include opacifying agents, such as film pigments, that can help the film in masking stains along the absorbent article 100 side edges, thereby serving as a masking element. In such a fashion, the film layer can serve to limit visualization of a fluid insult stain along the absorbent article 100 side edges when viewed from above the topsheet layer 110. The film layer may also serve as a barrier layer to prevent rewet of the topsheet layer 110 as well as to prevent the flow of fluid off the side edges of the absorbent article 100. In various embodiments, the side portions can be laminates such as a spunbond-meltblown-meltblown-spunbond layer ("SMMS") laminate, spunbond-film laminate, or alternatively, other nonwoven laminate combinations.

Absorbent System:

The absorbent system 120 can include at least an intake and distribution layer 122. In various embodiments, the absorbent system 120 can further include an absorbent core 124. It is to be understood that the absorbent system 120 can have additional elements, such as, but not limited to, a surge layer, a distribution layer, and/or a fluid intake layer, as are known to one of ordinary skill in the art.

The intake and distribution layer 122 can be placed below the topsheet layer 110 in the depth direction (Z) of the absorbent article 100. The intake and distribution layer 122 can be the foam and fiber composite 10 as described herein. The foam and fiber composite 10 is orientated such that the second planar surface 24 and individual fibers 32 of the fibrous material 30 which have been inserted into the foam material 10 are in proximity to the topsheet layer 110 and the exterior surface 34 of the fibrous material 30 is in proximity to the backsheet layer 112. In such an orientation of the foam and fiber composite 10 the fibers 32 which have extended through the foam material 20 and to the second planar surface 24 of the foam material 20 are in position to be presented to body exudates as they are received by the absorbent article 100. As the fibers 32 can be hydrophilic, they can provide hydrophilic pathways through the foam material 20 for the body exudates to pass through the foam material 20 from the second planar surface 24 to the first planar surface 22 and the fibrous material 30. Thus, the fibers 32 can provide for intake of the body exudates. The fibrous material 30 can, in various embodiments, provide sufficient storage capability to the absorbent article 100 to enable storage of the body exudates without the need of any additional layer of absorbent material positioned below the intake and distribution layer 122 in the depth direction (Z) of the absorbent article 100. In various embodiments in which an absorbent core 124 is also present in the absorbent system 120 the absorbent core 124 can be positioned between the intake and distribution layer 122 and the backsheet layer 112. The fibrous material 30, in its proximity to the absorbent core 124, can provide for distribution of the body exudates to the absorbent core 124 of the absorbent article 100. In various embodiments, the fibers 32 forming the fibrous material 30 on the first planar surface 22 of the foam and fiber composite 10 can be oriented in the longitudinal direction L of the absorbent article 100. In such an orientation of the fibers 32 of the fibrous material 30, the body exudates can be distributed in the longitudinal direction L of the absorbent article 100 through the hydrophilic capillary action of the fibers 32. The foam material 20 of the foam and fiber composite 10, as a hydrophobic material, can reduce and/or prevent the migration of the body exudates back towards the topsheet layer 110 of the absorbent article 100.

In various embodiments in which an absorbent core 124 is present, the absorbent core 124 can be positioned beneath the intake and distribution layer 122 in the depth direction of the absorbent article 100. The absorbent core 124 can generally be any single layer structure or combination of layer components, which can demonstrate some level of compressibility, conformability, be non-irritating to a wearer's skin, and capable of absorbing and retaining liquids and other body exudates. Additionally, the absorbent core 124 can provide additional capacity to absorb and retain body exudates such as menses. In various embodiments, the absorbent core 124 can be formed from a variety of different materials and can contain any number of desired layers. For example, the absorbent core 124 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily softwood fibers.

In various embodiments, if desired, the absorbent core 124 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 124 in any amount as desired.

Regardless of the combination of absorbent materials used in the absorbent core 124, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 124 can vary as desired and can comprise any one of various shapes including, but not limited to, triangular, rectangular, dog-bone and elliptical shapes. In various embodiments, the absorbent core 124 can have a shape that generally corresponds with the overall shape of the absorbent article 100. The dimensions of the absorbent core 124 can be substantially similar to those of the absorbent article 100, however, it will be appreciated that the dimensions of the absorbent core 124 while similar, will often be less than those of the overall absorbent article 100, in order to be adequately contained therein.

By way of example, suitable materials and/or structures for the absorbent core 124 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

In various embodiments, an absorbent core 124 can be a single layer structure and can include, for example, a matrix of cellulosic fluff and superabsorbent material. In various embodiments, an absorbent core 124 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 100 with different absorption properties as deemed suitable. In various embodiments, the body facing layer of the absorbent core 124 may be constructed of an airlaid material and the garment facing layer of the absorbent core 124 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Backsheet Layer:

The backsheet layer 112 is generally liquid impermeable and is the portion of the absorbent article 100 which faces the garment of the wearer. The backsheet layer 112 can permit the passage of air or vapor out of the absorbent article 100 while still blocking the passage of liquids. Any liquid impermeable material may generally be utilized to form the backsheet layer 112. The backsheet layer 112 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 112 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 112 can be a polyethylene film such as that obtainable from Berry Plastics, Evansville, IN, USA. Another example can include calcium carbonate-filled polypropylene film. In still another embodiment, the backsheet layer 112 can be a hydrophobic nonwoven material with water barrier properties such as a nonwoven laminate, an example of which can be a spunbond, meltblown, meltblown, spunbond, four-layered laminate. The backsheet layer 104 can, therefore, be of a single or multiple layer construction, such as of multiple film layers or laminates of film and nonwoven fibrous layers. Suitable backsheet layers 112 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Method to Calculate Proportion of Fibers within Foam Material:

The percentage of fiber 32 insertion thru the foam material 20 of a foam and fiber composite 10 can be determined by using the image analysis measurement method described herein. In this context, fiber 32 insertion is considered within each one-third of the cross-sectional thickness of the foam and fiber composite 10. Generally, the image analysis method determines a numeric value of percent fiber area, relative to both fiber and foam components, within each one-third of the foam and fiber composite's thickness via specific image analysis measurement parameters such as area. The percent fiber insertion method is performed using x-ray Micro-computed Tomography (a.k.a. Micro-CT) to non-destructively acquire images with subsequent image analysis techniques to detect both fiber and foam components separately and then calculating the percentages of each within the one-third divisions of the foam and fiber composite's thickness. To differentiate between fiber and foam components for subsequent detection and measurement, an image analysis algorithm is used which includes specific image analysis processing and measurement steps. The image analysis algorithm, performs detection, image processing and measurement and also transmits data digitally to a spreadsheet database. The resulting measurement data are used to compare the percent fiber of differing structures possessing both foam and fiber components.

The method for determining the percent fiber 32 in each one-third of the foam and fiber composite's 10 cross-sectional thickness includes the first step of acquiring digital x-ray Micro-CT images of a sample. These images are acquired using a SkyScan 1272 Micro-CT system available from Bruker microCT (2550 Kontich, Belgium). The foam and fiber composite 10 sample is attached to a mounting apparatus, supplied by Bruker with the SkyScan 1272 system, so that it will not move under its own weight during the scanning process. The following SkyScan 1272 conditions are used during the scanning process:

Camera Pixel Size (um)=9.0
Source Voltage (kV)=40
Source Current (uA)=250
Image Pixel Size (um)=4.0
Image Format=TIFF
Depth (bits)=16
Rotation Step (deg.)=0.200
Use 360 Rotation=NO
Frame Averaging=ON (5)
Random Movement=ON (2)
Flat Field Correction=ON
Filter=No Filter After sample scanning is completed, the resulting image set needs to be reconstructed using the NRecon program provided with the SkyScan 1272 Micro-CT system. While reconstruction parameters can be somewhat sample dependent, and should be known to those skilled in the art, the following parameters should provide a basic guideline to an analyst:

Image File Type=BMP
Pixel Size (um)=4.00
Smoothing=0
Ring Artifact Correction=7
Beam Hardening Correction (%)=20

After reconstruction is completed, the resulting image data set is now ready for image analysis.

The image analysis software platform used to perform the percent fiber insertion measurements is a QWIN Pro (Version 3.5.1) available from Leica Microsystems, having an office in Heerbrugg, Switzerland.

Thus, the method for determining the percent fiber insertion of a given specimen includes the step of performing several area measurements on the Micro-CT image. Specifically, an image analysis algorithm is used to read and process images as well as perform measurements using Quantimet User Interactive Programming System (QUIPS) language. The image analysis algorithm is reproduced below.

The following line designates the computer location where data is sent to

Open File (D:\Data\z-data.xls, channel #1)
Initialize Variables
TOTFIELDS=0
FRAMEW=0
Image and Frames Setup
Calvalue=4 um/pixel
--CALVALUE=4.0
Calibration (Local)
Enter Results Header
File Results Header (channel #1)
File Line (channel #1)
The following three lines are based on the size of the reconstructed Micro-CT images
Configure (Image Store 2136×1040, Grey Images 51, Binaries 24)
Image frame (x 0, y 0, Width 2136, Height 512)
Measure frame (x 951, y 2, Width 1135, Height 509)
The following line is based on the image file prefix from the Micro-CT image set being analyzed.
PauseText ("Enter image prefix now.")
Input (TITLE$)
File (TITLE$, channel #1)
File Line (channel #1)
File ("Foam Area", channel #1)
File ("Pulp Area", channel #1)
File ("% foam (1/3)", channel #1)
File ("% Pulp (1/3)", channel #1)
File ("Foam Area", channel #1)
File ("Pulp Area", channel #1)
File ("% foam (2/3)", channel #1)
File ("% Pulp (2/3)", channel #1)
File ("Foam Area", channel #1)
File ("Pulp Area", channel #1)

File ("% foam (3/3)", channel #1)
File ("% Pulp (3/3)", channel #1)
File Line (channel #1)
Analysis Loop
The following line is based on the image file suffix numbers from the Micro-CT image set being analyzed.
For (REPLICATE=200 to 1200, step 20)
Image Acquistion and Detection
Grey Util (Clear All)
ACQOUTPUT=0
The following two lines indicate the computer location of the Micro-CT images to be read during the image analysis process.
ACQFILE$="D:\Images\sen_1016a1_Rec\"+TITLE$+ ""+STR$(REPLICATE)+".bmp"
Read image (from file ACQFILE$ into ACQOUTPUT)
Grey Transform (BSharpen from Image0 to Image1, cycles 3, operator Disc)
The following line is the gray-level threshold level for detecting the fiber and foam components within an image. The threshold may need to be adjusted prior to executing the algorithm to reflect optimal detection of both foam and fiber components.

```
Detect (whiter than 78, from Image1 into Binary0 delineated)
IMAGE PROCESSING
Binary Amend (Close from Binary0 to Binary1, cycles 1, operator Disc, edge
erode on)
MEASURE FEATURES for FEATURE ACCEPTANCE
Measure frame (x 951, y 2, Width 1135, Height 509)
Measure feature (plane Binary1, 8 ferets, minimum area: 4, grey image: Image1)
    Selected parameters: Area, X FCP, Y FCP, Length, Perimeter, Roundness,
    UserDef1, AspectRatio
Feature Accept:
    Roundness from 2.5 to 100.
    Area from 75. to 200000.
Copy Accepted Features (from Binary1 into Binary2)
BINARY LOGICAL
Binary Logical (C = A XOR B: C Binary3, A Binary1, B Binary2)
MEASUREMENTS - FOAM & PULP
Measure frame (x 951, y 2, Width 1135, Height 509)
MFLDIMAGE = 2
PauseText ("Manually measure the approximate thickness of the material.")
MANUALIN = 1
Manual Measurement [PAUSE] (plane MANUALIN, mode Distance, count
into MANUAL.COUNT, results into MANUAL.RESULTS(count,2), statistics
into MANUAL.STATS(7,2))
    Selected parameters: Y Coord, Height
YPOS = MANUAL.RESULTS(1,1)
HEIGHT = MANUAL.RESULTS(1,2)
ONETHIRD = INT(HEIGHT/3)
MFRAMEX = 950
MFRAMEW = 1135
MFRAMEH = ONETHIRD
MFRAMEY = YPOS
Display (Image1 (on), frames (on,on), planes (off,off,2,3,off,off), lut 5, x 0, y 0,
z 0, Reduction off)
Measure frame [PAUSE] (x MFRAMEX, y MFRAMEY, Width MFRAMEW,
Height MFRAMEH)
-- Upper 1/3 measurements
MFLDIMAGE = 2
Measure field (plane MFLDIMAGE, into FLDRESULTS(1), statistics into
FLDSTATS(7,1) )
    Selected parameters: Area
FOAMAREA = FLDRESULTS(1)
MFLDIMAGE = 3
Measure field (plane MFLDIMAGE, into FLDRESULTS(1), statistics into
FLDSTATS(7,1))
    Selected parameters: Area
PULPAREA = FLDRESULTS(1)
File (FOAMAREA, channel #1, 0 digits after '.')
File (PULPAREA, channel #1, 0 digits after '.')
File ("", channel #1)
File ("", channel #1)
-- Middle 1/3
MFRAMEY = MFRAMEY+ONETHIRD
Measure frame [PAUSE] (x MFRAMEX, y MFRAMEY, Width MFRAMEW,
Height MFRAMEH)
MFLDIMAGE = 2
Measure field (plane MFLDIMAGE, into FLDRESULTS(1), statistics into
FLDSTATS(7,1))
    Selected parameters: Area
FOAMAREA = FLDRESULTS(1)
MFLDIMAGE = 3
Measure field (plane MFLDIMAGE, into FLDRESULTS(1), statistics into
FLDSTATS(7,1))
    Selected parameters: Area
PULPAREA = FLDRESULTS(1)
File (FOAMAREA, channel #1, 0 digits after '.')
```

```
    File (PULPAREA, channel #1, 0 digits after '.')
    File ("", channel #1)
    File ("", channel #1)
    -- Lower 1/3
    MFRAMEY = MFRAMEY+ONETHIRD
    Measure frame [PAUSE] (x MFRAMEX, y MFRAMEY, Width
    MFRAMEW, Height MFRAMEH)
    MFLDIMAGE = 2
    Measure field (plane MFLDIMAGE, into FLDRESULTS(1), statistics into
    FLDSTATS(7,1))
         Selected parameters: Area
    FOAMAREA = FLDRESULTS(1)
    MFLDIMAGE = 3
    Measure field (plane MFLDIMAGE, into FLDRESULTS(1), statistics into
    FLDSTATS(7,1))
         Selected parameters: Area
    PULPAREA = FLDRESULTS(1)
    File (FOAMAREA, channel #1, 0 digits after '.')
    File (PULPAREA, channel #1, 0 digits after '.')
    File ("", channel #1)
    File ("", channel #1)
    File Line (channel #1)
Next (REPLICATE)
Close File (channel #1)
END
```

The QUIPS algorithm is executed using the QWIN Pro software platform. The analyst is initially prompted to enter the specimen set information which is sent to the EXCEL file.

The analyst is next prompted by an interactive command window and an input window to enter the image file prefix of the Micro-CT images to be analyzed. After this step, all subsequent images for a given sample will be read automatically by the image analysis algorithm described above.

The analyst is next prompted to manually measure the approximate thickness of the sample cross-section as viewed in the image window. This is performed by using the computer mouse to draw a straight line between the upper and lower surface planes of the sample cross-section. After a single line has been drawn, the analyst then continues the image analysis algorithm by clicking on the 'OK' or 'Continue' buttons shown on the screen. A similar prompting will occur for all subsequent images automatically read by the algorithm.

After the image analysis algorithm automatically performs several binary image processing steps and the measurement step on the detected binaries of the foam and fiber components and exports the corresponding data to the designated EXCEL spreadsheet file, the image analysis algorithm will automatically read the next image and prompt the analyst to again manually measure the thickness of the media in the current image being processed. This process is repeated until all of the designated images have been analyzed.

The following measurement parameter data will be located in the EXCEL file for each of the one-thirds of the foam and fiber composite's thickness after measurements and data transfer have occurred:

Foam Area

Pulp Area

There will be three pairs of foam and fiber data shown in the spreadsheet at the completion of the analysis. The left-most pair will correspond to the upper one-third of the foam and fiber composite 10 thickness as shown in the images, the center pair will correspond to the middle one-third, and the right-most pair will correspond to the lower one-third. Using these data, the analyst can easily set-up additional columns in the EXCEL spreadsheet for calculating the percentages of both foam and pulp in each of the three one-third divisions of the foam and fiber composite's thickness. It is recommended that the analyst perform the analysis on a foam material only sample to act as a 'blank' for percent fibers which can then be subtracted from actual samples containing both foam and fibers.

Multiple sampling replicates from a single specimen can be performed during a single execution of the QUIPS algorithm from reading in multiple images (Note: The REPLICATE For—Next line in the algorithm needs to be adjusted to reflect the number of sample replicate analyses to be performed per specimen). For example, from a Micro-CT image set of 1000 images, every 20th image can be analyzed resulting in 50 data points per sample. A comparison between different samples can be performed using a Student's T analysis at the 90% confidence level.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A process for manufacturing a foam and fiber composite, the process comprising the steps of:
   a. providing a foam material comprising a first planar surface and a second planar surface;
   b. providing a fluid treatment device having a pressurized fluid jet capable of emitting a pressurized fluid stream of fluid from the pressurized fluid jet in a direction towards the foam material;
   c. directing the pressurized fluid stream of fluid in a direction from the pressured fluid jet of the fluid treatment device towards the first planar surface of the foam material;
   d. after directing the pressurized fluid stream of fluid towards the first planar surface of the foam material, providing a fibrous material comprising a plurality of individual fibers and layering the fibrous material onto the first planar surface of the foam material to form a layered composite;
   e. providing a fluid insertion device having a pressurized fluid jet capable of emitting a pressurized fluid stream of fluid from the pressurized fluid jet in a direction towards the layered composite; and
   f. directing the pressurized fluid stream of fluid in a direction from the pressurized fluid jet of the fluid insertion device towards the fibrous material of the layered composite to cause a portion of the plurality of individual fibers of the fibrous material to be directed into the foam material to form the foam and fiber composite;
   wherein the pressure of the fluid of the pressurized fluid streams of the fluid treatment device is from 150 psi to 1000 psi.

2. The process of claim 1 further comprising the step of providing a support belt.

3. The process of claim 2 wherein the support belt is a single plain weave foraminous wire.

4. The process of claim 1 wherein a strain rate is maintained on the foam material at less than about 5% strain.

5. The process of claim 1 wherein the pressure of the fluid of the pressurized fluid streams of the fluid treatment device is from about 150 psi to about 1000 psi.

6. The process of claim 1 wherein the pressure of the fluid of the pressurized fluid streams of the fluid insertion device is from about 70 psi to about 1000 psi.

7. The process of claim 1 wherein the foam material has a permeability to air flow of less than about 200 CFM prior to contact by the fluid of the pressurized fluid streams of the fluid treatment device and a permeability to air flow of greater than about 600 CFM following contact by the fluid of the pressurized fluid streams of the fluid treatment device.

8. The process of claim 1 wherein a plurality of individual fibers are present at the second planar surface of the foam material following contact by the fluid of the pressurized fluid streams of the fluid insertion device.

9. The process of claim 1 wherein the foam material has an elongation at break of less than about 200%.

10. The process of claim 9 wherein the foam material has an elongation at break of from about 80% to about 200%.

11. A foam and fiber composite manufactured according to the process of claim 1.

12. The foam and fiber composite of claim 11 wherein the foam and fiber composite has a permeability to air flow greater than about 300 CFM.

13. The foam and fiber composite of claim 11 wherein the foam material has a height measured from the first planar surface to the second planar surface and from about 15% to about 25% of fibers are present throughout the height of the foam material.

14. An absorbent article comprising a topsheet layer, a backsheet layer, and an absorbent system positioned between the topsheet layer and the backsheet layer, wherein the absorbent system comprises the foam and fiber composite of claim 11.

15. The foam and fiber composite of claim 11 wherein the foam material is a polyester polyurethane foam.

16. The foam and fiber composite of claim 11 wherein the fibers of the fibrous material are cellulosic fibers.

17. The foam and fiber composite of claim 11 wherein the total basis weight of the foam and fiber composite is from about 20 gsm to about 250 gsm.

18. The foam and fiber composite of claim 11 wherein the basis weight of the fibrous material is at least about 10% of the total basis weight of the foam and fiber composite.

* * * * *